(12) United States Patent
Chen et al.

(10) Patent No.: US 9,187,439 B2
(45) Date of Patent: Nov. 17, 2015

(54) TRICYCLIC COMPOUNDS USEFUL AS NEUROGENIC AND NEUROPROTECTIVE AGENTS

(71) Applicant: INCEPTION 1, INC., San Diego, CA (US)

(72) Inventors: Austin Chih-Yu Chen, San Marcos, CA (US); Jill Melissa Baccei, Poway, CA (US); Brian Andrew Stearns, Encinitas, CA (US); Nicholas Simon Stock, Encinitas, CA (US); Yen Pham Truong, San Diego, CA (US)

(73) Assignee: Inception Orion, Inc., San Diego, CA (US)

( * ) Notice: Subject to any disclaimer, the term of this patent is extended or adjusted under 35 U.S.C. 154(b) by 0 days.

(21) Appl. No.: 14/345,914

(22) PCT Filed: Sep. 19, 2012

(86) PCT No.: PCT/US2012/056143
§ 371 (c)(1),
(2) Date: Mar. 19, 2014

(87) PCT Pub. No.: WO2013/043744
PCT Pub. Date: Mar. 28, 2013

(65) Prior Publication Data
US 2014/0243313 A1   Aug. 28, 2014

Related U.S. Application Data

(60) Provisional application No. 61/537,471, filed on Sep. 21, 2011.

(51) Int. Cl.
| C07D 279/20 | (2006.01) |
| C07D 487/10 | (2006.01) |
| C07D 491/107 | (2006.01) |
| C07D 279/28 | (2006.01) |

(52) U.S. Cl.
CPC ............ *C07D 279/28* (2013.01); *C07D 487/10* (2013.01); *C07D 491/107* (2013.01)

(58) Field of Classification Search
CPC . C07D 279/20; C07D 491/107; C07D 487/10
USPC .............................. 514/210.21, 225.2; 544/46
See application file for complete search history.

(56) References Cited

U.S. PATENT DOCUMENTS

| 2,814,622 A | 11/1957 | Moffett |
| 2,933,495 A | 4/1960 | Heinzelman et al. |
| 2,945,030 A | 7/1960 | Maxwell |
| 2,956,996 A | 10/1960 | Craig |
| 3,082,210 A | 3/1963 | Jacob |
| 3,084,160 A | 4/1963 | Michel et al. |
| 3,359,265 A | 12/1967 | Jucker et al. |
| 3,574,204 A | 4/1971 | Nakanishi et al. |
| 3,737,537 A | 6/1973 | Hayden |
| 4,249,002 A | 2/1981 | Eriksoo |
| 4,249,003 A | 2/1981 | Eriksoo |
| 4,407,800 A | 10/1983 | Pearson et al. |
| 4,425,337 A | 1/1984 | Alexander et al. |
| 4,851,325 A | 7/1989 | Morimoto |
| 6,054,453 A | 4/2000 | Lohray et al. |
| 6,172,058 B1 | 1/2001 | Tercero et al. |

(Continued)

FOREIGN PATENT DOCUMENTS

| DE | 974062 | 9/1960 |
| DE | 10339157 | 3/2005 |

(Continued)

OTHER PUBLICATIONS

Hoerlien et al., Pharmacological comparison of phenoxazine and phenothiazine compounds, STN Database accession No. 1964-406953, Med. Chem., Abhandl. Med.-Chem Forschungsstaetten Farbenfabriken Bayer, 7:79-98, 1963.
Extended European Search Report dated Feb. 6, 2015 in patent application No. 12833258.2.
Gasiorwski et al. Antimutagenic activity of new analogues of fluphenazine. Cellular & Molecular Biology Letters 8:927-942 (2003).
Moffet et al. Aminoalkylphenothiazines. Journal of the American Chemical Society 82:1600-1607 (1960).

(Continued)

*Primary Examiner* — Kahsay Habte
(74) *Attorney, Agent, or Firm* — Knobbe, Martens, Olson & Bear LLP

(57) ABSTRACT

The invention disclosed herein is direct to compounds of Formula I and pharmaceutically acceptable salts thereof, which are useful in treating neurodegenerative diseases and promoting the generation or survival of neurons in the mammalian brain. The invention also comprises pharmaceutical compositions comprising a therapeutically effective amount of compound of Formula I or a pharmaceutically acceptable salt thereof. The invention disclosed herein is also directed to a method of promoting the generation or survival of neurons in a patient in need thereof in neurodegenerative and related diseases.

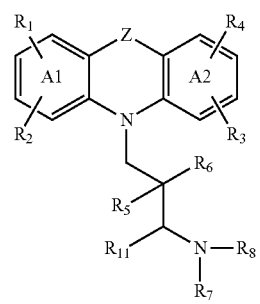

8 Claims, No Drawings

(56) References Cited

U.S. PATENT DOCUMENTS

| | | |
|---|---|---|
| 6,191,165 B1 | 2/2001 | Ognyanov et al. |
| 6,249,369 B1 | 6/2001 | Theiste et al. |
| 6,440,961 B1 | 8/2002 | Lohray et al. |
| 7,189,483 B2 | 3/2007 | Danilevecius |
| 7,241,319 B2 | 7/2007 | Lagrange |
| 7,348,116 B2 | 3/2008 | Matoliukstyte et al. |
| 7,364,825 B2 | 4/2008 | Lygaitis |
| 7,648,777 B2 | 1/2010 | Park et al. |
| 2006/0035863 A1 | 2/2006 | Barbeau |
| 2006/0235001 A1 | 10/2006 | Elliott et al. |
| 2010/0055183 A1 | 3/2010 | Ellies et al. |
| 2011/0003836 A1 | 1/2011 | McKnight et al. |

FOREIGN PATENT DOCUMENTS

| | | |
|---|---|---|
| EP | 309422 | 1/1990 |
| EP | 117302 | 6/1990 |
| EP | 535672 | 1/2001 |
| EP | 1 094 063 A1 | 4/2001 |
| EP | 1 470 818 A1 | 10/2004 |
| FR | 1267515 | 7/1961 |
| FR | 1363290 | 5/1964 |
| FR | 1368918 | 6/1964 |
| FR | 1381437 | 11/1964 |
| FR | 2791687 | 10/2000 |
| GB | 883324 | 11/1961 |
| JP | H07216352 | 8/1995 |
| JP | H08119920 | 5/1996 |
| JP | H11130772 | 5/1999 |
| JP | 2007176851 | 7/2007 |
| JP | 2008001827 | 1/2008 |
| JP | 2008019224 | 1/2008 |
| KR | 102011030909 | 3/2011 |
| WO | WO94/21616 | 9/1994 |
| WO | WO97/33871 | 9/1997 |
| WO | WO97/45115 | 12/1997 |
| WO | WO98/11923 | 3/1998 |
| WO | WO98/52946 | 11/1998 |
| WO | WO99/19313 | 4/1999 |
| WO | WO00/32175 | 6/2000 |
| WO | WO00/50414 | 8/2000 |
| WO | WO00/59884 | 10/2000 |
| WO | WO02/22130 | 6/2002 |
| WO | WO03/043985 | 5/2003 |
| WO | WO03/062388 | 7/2003 |
| WO | WO2004/037192 | 5/2004 |
| WO | WO2004/103995 | 12/2004 |
| WO | WO2005/005421 | 1/2005 |
| WO | WO2005/016919 | 2/2005 |
| WO | WO2005/026134 | 3/2005 |
| WO | WO2005/027842 | 3/2005 |
| WO | WO2005/105145 | 11/2005 |
| WO | WO2006/052930 | 5/2006 |
| WO | WO2006/117760 | 11/2006 |
| WO | WO2007/025709 | 3/2007 |
| WO | WO2007/062862 | 6/2007 |
| WO | WO2008/009935 | 1/2008 |
| WO | WO2008/055068 | 5/2008 |
| WO | WO2008/103320 | 8/2008 |
| WO | WO2009/023299 | 2/2009 |
| WO | WO2009/137462 | 11/2009 |
| WO | WO2009/141627 | 11/2009 |
| WO | WO2010/033643 | 3/2010 |
| WO | WO2010/042489 | 4/2010 |
| WO | WO2010/088340 | 8/2010 |
| WO | WO2010/119275 | 10/2010 |
| WO | WO2011/015875 | 2/2011 |
| WO | WO2011/025969 | 3/2011 |
| WO | WO2013/043744 | 3/2013 |

OTHER PUBLICATIONS

PCT/US2012/056143 International Preliminary Report on Patentability dated Mar. 25, 2014.
PCT/US2012/056143 International Search Report and Written Opinion dated Mar. 28, 2013.
PubChem CID 21235187. Dec. 5, 2007.
Testa et al. Substances acting on the central nervous system. XVI. The chemistry of 3,3-disubstituted azetidine. Justus Liebigs Annalen der Chemie 635:119-27 (1960).

TRICYCLIC COMPOUNDS USEFUL AS NEUROGENIC AND NEUROPROTECTIVE AGENTS

RELATED APPLICATIONS

This application is filed pursuant to 35 U.S.C. 371 as a U.S. National Phase Application of International Application No. PCT/US2012/056143, entitled "TRICYCLIC COMPOUNDS USEFUL AS NEUROGENIC AND NEUROPROTECTIVE AGENTS", filed Sep. 19, 2012, which claims the benefit of U.S provisional patent application no. 61/537,471 entitled "TRICYCLIC COMPOUNDS USEFUL AS NEUROGENIC AND NEUROPROTECTIVE AGENTS" filed on Sep. 21, 2011, each of which is incorporated by reference in its entirety.

FIELD OF THE INVENTION

This invention is directed to novel compounds, or pharmaceutically acceptable salts thereof, that promote neurogenesis, neuroprotection and/or retard neuronal cell death.

BACKGROUND OF THE INVENTION

Therapeutically effective treatment of neurodegenerative diseases continues to be an area of unmet medical need. In the face of an aging population throughout the industrialized nations, this need will continue to grow for the foreseeable future. In 2010, the CDC estimated that by the year 2030, the U.S. population over 65 will double to about 71 million.

Opportunities for small molecule therapeutic intervention are promising. It is now accepted that the adult vertebrate brain fosters the birth and functional incorporation of newly formed neurons (Goldman and Nottebohm, 1984; Paton and Nottebohm, 1984; Burd and Nottebohm, 1985). It is also now accepted that within all mammalian species, including humans (Eriksson et al., 1998), there are two major reservoirs of neuronal stem cells, one located in the subgranular zone (SGZ) of the hippocampal dentate gyrus and another in the subventricular zone (SVZ) (Gross, 2000). Neural stem cells in the SVZ facilitate formation of new neurons that migrate rostrally to populate the olfactory bulb, while neural stem cells in the SGZ produce neurons that integrate locally in the granular layer of the dentate gyrus, a region of the hippocampus that exhibits lifelong structural and functional plasticity.

Bombrun, et. al., J. Med. Chem., 2003, Vol. 46, No. 21, 4365-68, discloses small molecules which, in isolated mitochondria prevent cytochrome c release induced by the BH3 only protein BID. This effect was suggested to be related to the molecule's ability to prevent permeabilization of the outer mitochondrial membrane. This effect was confirmed by Peixoto in 2009 demonstrating that such compounds do indeed inhibit mitochondrial permeabilization by preventing the formation of mitochondrial apoptosis channels (MAC) (Peixoto, et al., Biochem J, 2009, 423, 381-387). Pieper, et. al., Cell 142, 39-51, Jul. 9, 2010, provides evidence that small molecule P7C3 exerts proneurogenic activity by preventing apoptosis of "newborn" hippocampal neurons. And Sachdeva and Burns, CNS Neuroscience & Therapeutics, Vol. 17 (2010) 199-205, reviewed Dimebolin, a small molecule nonselective anti-histamine, which in some studies appears to have had beneficial effects on several symptoms of Alzheimer's type dementia.

Apoptosis plays a substantial role in cell death that occurs in conjunction with various disease and injury conditions. For example, apoptosis leads to neuronal loss associated with neurodegenerative disorders, including Alzheimer's disease (Barinaga, Science 281:1303-1304), Huntington's disease, spinal-muscular atrophy, stroke (reviewed in Rubin, British Med. Bulle., 53(3):617-631, 1997; and Barinaga, Science 281:1302-1303), and transient ischemic neuronal injury, as in spinal cord injury. Accordingly, it would be of great benefit to prevent undesired apoptosis in these various diseases and injury situations.

The mitochondrial apoptosis-induced channel, MAC, is induced early in apoptosis (Pavlov, E. V., Priault, M., Pietkiewicz, D., Cheng, E. H., Antonsson, B., Manon, S., Korsmeyer, S. J., Mannella, C. A. and Kinnally, K. W. (2001), J Cell Biol 155, 725-31). The high conductance (2-6 nS) suggests MAC has a pore that is >4 nm in diameter. Evidence is mounting that MAC provides the pathway through the outer membrane for release of the 3.3 nm diameter cytochrome c. Not only does cytochrome c reduce the conductance of MAC in a manner consistent with its partitioning into the pore of MAC (Guo, L., Pietkiewicz, D., Pavlov, E. V., Grigoriev, S. M., Kasianowicz, J. J., Dejean, L. M., Korsmeyer, S. J., Antonsson, B. and Kinnally, K. W. (2004), Am J Physiol Cell Physiol 286, C1109-17), but proteoliposomes expressing MAC activity fail to retain cytochrome c. MAC activity is present in multiple different cell types (CSM14.1, and various clones of FL5.12 and HeLa cells) during cytochrome c release. More recently, Peixoto, P. M., et. al., Biochem. J. (2009), 423, 381-387 discloses MAC inhibitors that suppress mitochondrial apoptosis. It is our belief that inhibiting or preventing the formation or the opening of MAC may, therefore, retard or prevent neurodegeneration.

SUMMARY OF THE INVENTION

The invention disclosed herein is direct to compounds of Formula I

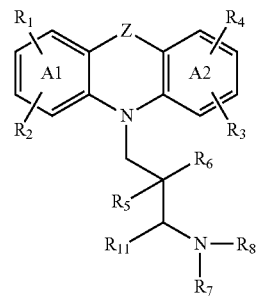

and pharmaceutically acceptable salts thereof, which are useful in treating neurodegenerative diseases and promoting the generation or survival of neurons in the mammalian brain. The invention also comprises pharmaceutical compositions comprising a therapeutically effective amount of compound of Formula I, or a pharmaceutically acceptable salt thereof. The invention disclosed herein is also directed to a method of promoting the generation or survival of neurons in a patient in need thereof in neurodegenerative and related diseases.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

In one aspect the invention is directed to a compound of Formula I

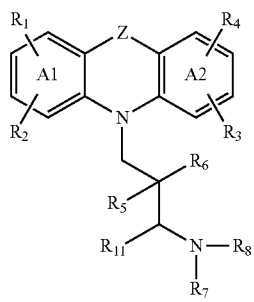

Formula I or a pharmaceutically acceptable salt thereof wherein:

A1 and A2 are each independently phenyl or a 6 membered heteroaromatic ring having 1, 2 or 3 N atoms in the heteroaromatic ring;

Z is selected from the group consisting of $CH_2$, NH, NR, O, S, $S(O)_2$, $C(Me)_2$, and C(O);

R is selected from the group consisting of
  (a) $CF_3$,
  (b) $C_{1-6}$ alkyl,
  (c) $-S(O)_2C_{1-4}$ alkyl,
  (d) $-C(O)C_{1-4}$alkyl,
  (e) $C_{3-6}$ cycloalkyl,
  (f) $-C(O)C_{3-6}$ cycloalkyl,
  (g) $-S(O)_2C_{3-6}$ cycloalkyl,
  (h) $-C(O)_2C_{1-4}$alkyl,
  (i) $-C(O)_2C_{3-6}$cycloalkyl,
  (j) aryl, and
  (k) heteroaryl,
wherein the alkyl portion of choices (b), (c), (d) and (h) and the cycloalkyl portion of choices (e), (f), (g) and (i) is optionally substituted with halo, and
wherein the aryl of choice (j) and the heteroaryl of choice (k) are each optionally mono or di-substituted with substituents selected from halogen, nitro, $C_{1-6}$alkyl, $C_{1-6}$ alkoxy, halo$C_{1-6}$alkyl, $C_{3-6}$cycloalkyl, $C_{3-6}$cycloalkoxy, $-NH(C_{1-6}$alkyl), $-NH(C_{3-6}$cycloalkyl), $-N(C_{1-6}$alkyl$)_2$, $-N(C_{3-6}$cycloalkyl$)_2$, $-S(O)_nC_{1-6}$alkyl, $-S(O)_nC_{3-6}$cycloalkyl and CN;

$R_1$, $R_2$, $R_3$ and $R_4$ are each independently selected from the group consisting of
  (a) hydrogen,
  (b) halogen,
  (c) CN,
  (d) $CF_3$,
  (e) $C_{1-6}$alkyl,
  (f) $C_{1-6}$ alkoxy,
  (g) $-S(O)_nC_{1-6}$ alkyl,
  (h) $-NH(C_{1-6}$ alkyl),
  (i) $-N(C_{1-6}$ alkyl$)_2$,
  (j) $-NHC(O)(C_{1-6}$alkyl),
  (k) $-NHS(O)_2C_{1-6}$ alkyl,
  (l) $-NHS(O)_2$ aryl,
  (m) $-C_{3-6}$ cycloalkyl,
  (n) $-C_{3-6}$ cycloalkoxy,
  (o) $-S(O)_nC_{3-6}$cycloalkyl,
  (p) $-NH(C_{3-6}$cycloalkyl),
  (q) $-N(C_{3-6}$ cycloalkyl$)_2$,
  (r) $-NHS(O)_2C_{3-6}$cycloalkyl,
  (s) $-C(O)C_{3-6}$cycloalkyl,
  (t) $-C(O)C_{1-6}$alkyl,
  (u) aryl,
  (v) heteroaryl,
  (w) $-S(O)_nNR_{12}R_{13}$, and
  (x) $-C(O)NR_{12}R_{13}$,
wherein the alkyl portion of choices (e), (f), (g), (h), (i), (j), (k) and (t) and the cycloalkyl portion of choices (m), (o), (p), (q), (r) and (s) is optionally substituted with halo, and
wherein aryl choice (u) and heteroaryl of choice (v) are each optionally mono or di-substituted with substituents selected from halogen, nitro, $C_{1-6}$alkyl, $C_{1-6}$ alkoxy, halo $C_{1-6}$alkyl, $C_{3-6}$cycloalkyl, $C_{3-6}$cycloalkoxy, $-NH(C_{1-6}$alkyl), $-NH(C_{3-6}$cycloalkyl), $-N(C_{1-6}$alkyl$)_2$, $-N(C_{3-6}$cycloalkyl$)_2$, $-S(O)_nC_{1-6}$alkyl, $-S(O)_nC_{3-6}$cycloalkyl and CN;

$R_5$ is selected from the group consisting of:
  (a) hydrogen,
  (b) F,
  (c) $C_{1-6}$alkyl, and
  (d) $C_{3-6}$cycloalkyl;

$R_6$ is selected from the group consisting of:
  (a) hydrogen,
  (b) F,
  (c) hydroxyl,
  (d) $-C_{1-6}$alkyl,
  (e) $-S(O)_nC_{1-6}$ alkyl,
  (f) $-C(O)C_{1-6}$alkyl,
  (g) $-OC_{1-6}$alkyl,
  (h) $-NH_2$;
  (i) $-NH(C_{1-6}$alkyl),
  (j) $-N(C_{1-6}$ alkyl$)_2$,
  (k) $C_{3-6}$cycloalkyl,
  (l) $-C(O)C_{3-6}$ cycloalkyl,
  (m) $-S(O)_nC_{3-6}$ cycloalkyl,
  (n) $-OC_{3-6}$ cycloalkyl,
  (o) $-NH(C_{3-6}$ cycloalkyl), and
  (p) $-N(C_{3-6}$cycloalkyl$)_2$,
or $R_5$ and $R_6$ together with the carbon to which they are attached forms a $C_{3-6}$cycloalkyl, or an optionally mono-substituted 4, 5 or 6 membered saturated or partially unsaturated heterocycloalkyl ring having 1 or 2 heteroatoms selected from N, $S(O)_n$ and O, wherein the substituent is selected from halogen, hydroxyl, nitro, oxo, $C_{1-6}$alkyl, $C_{1-6}$ alkoxy, halo$C_{1-6}$alkyl, $C_{3-6}$cycloalkyl, $C_{3-6}$cycloalkoxy, $-NH(C_{3-6}$cycloalkyl), $-N(C_{3-6}$cycloalkyl$)_2$, $-S(O)_nC_{1-6}$alkyl, $-S(O)_nC_{3-6}$cycloalkyl, aryl, heteroaryl, CN, $-NHS(O)_nC_{1-6}$alkyl, $-NHS(O)_n$aryl, $-N(R_{12})(S(O)_n)C_{1-6}$alkylaryl and $-CO_2NR_{12}R_{13}$;

$R_7$ is hydrogen;

$R_8$ is selected from aryl, heteroaryl and heterocycle, wherein said aryl, heteroaryl and heterocycloalkyl are each optionally mono or di-substituted with substituents selected from halogen, hydroxyl, nitro, $C_{1-6}$alkyl, $C_{1-6}$ alkoxy, halo $C_{1-6}$alkyl, $C_{3-6}$cycloalkyl, $C_{3-6}$cycloalkoxy, $-NR_{12}R_{13}$, $-NH(C_{3-6}$cycloalkyl), $-N(C_{3-6}$cycloalkyl$)_2$, $-S(O)_n C_{1-6}$alkyl, $-S(O)_nC_{3-6}$cycloalkyl, aryl, heteroaryl, and CN;

or $R_5$ and $R_7$ are joined together so that together with the nitrogen to which $R_7$ is attached there is formed an optionally mono-substituted 4, 5 or 6 membered saturated or partially unsaturated heterocycloalkyl ring having 1 or 2 heteroatoms selected from N, $S(O)_n$ and O, wherein the substituent is selected from halogen, hydroxyl, nitro, oxo, $C_{1-6}$alkyl, $C_{1-6}$ alkoxy, halo$C_{1-6}$alkyl, $C_{3-6}$cycloalkyl, $C_{3-6}$cycloalkoxy, $-NH(C_{3-6}$cycloalkyl), $-N(C_{3-6}$cycloalkyl)$_2$, —S(O)$_n$C$_{1-6}$alkyl, —S(O)$_n$C$_{3-6}$cycloalkyl, aryl, heteroaryl, CN, —NHS(O)$_n$C$_{1-6}$alkyl, —NHS(O)$_n$aryl, —N(R$_{12}$)(S(O)$_n$)C$_{1-6}$alkylaryl and CO$_2$NR$_{12}$R$_{13}$;

or R$_7$ and R$_8$ are joined together so that together with the nitrogen to which they are attached there is formed a 4, 5 or 6 membered saturated or unsaturated monocyclic heterocyclic ring or a 6 to 12 membered saturated or unsaturated bicyclic heterocyclic ring, said monocyclic or bicyclic ring having 1 or 2 heteroatoms selected from N, S(O)$_n$ and O, and said monocyclic or bicyclic ring is optionally substituted with 1 to 4 substituents selected from R$_9$, R$_{10}$, R$_{15}$ and R$_{16}$;

R$_9$ is hydrogen; and

R$_{10}$ is selected from halogen, hydroxyl, nitro, C$_{1-6}$alkyl, —C$_{1-6}$alkylaryl, C$_{1-6}$ alkoxy, haloC$_{1-6}$alkyl, C$_{3-6}$cycloalkyl, C$_{3-6}$cycloalkoxy, —NR$_{12}$R$_{13}$, —NCONR$_{12}$R$_{13}$, —NH(C$_{3-6}$cycloalkyl), —N(C$_{1-6}$alkyl)$_2$, —N(C$_{3-6}$cycloalkyl)$_2$, —S(O)$_n$C$_{1-6}$alkyl, —S(O)$_n$C$_{3-6}$cycloalkyl, aryl, heteroaryl, CN, phenyloxy, —NHS(O)$_n$C$_{1-6}$alkyl, —NHS(O)$_2$aryl, —N(R$_{12}$)(S(O)$_n$)alkylaryl, —CONR$_{12}$R$_{13}$ and hydroxyC$_{1-6}$alkyl, wherein said aryl or said phenyl is optionally mono-substituted with halogen, nitro, C$_{1-6}$alkyl, C$_{1-6}$ alkoxy, halo C$_{1-6}$alkyl, C$_{3-6}$cycloalkyl, or C$_{3-6}$cycloalkoxy; or R$_9$ and R$_{10}$ joined together with the atoms connecting R$_9$ and R$_{10}$ form a C$_{3-6}$cycloalkyl, or a 4, 5 or 6 membered saturated or unsaturated monocyclic heterocyclic ring or a 6 to 12 membered saturated or unsaturated bicyclic heterocyclic ring, said monocyclic or bicyclic ring having 1 or 2 heteroatoms selected from N, S(O)$_n$ and O, and said C$_{3-6}$cycloalkyl, monocyclic or bicyclic heterocyclic ring is optionally mono or di-substituted with substituents are independently selected from the group consisting of (a) halogen,
(b) hydroxyl,
(c) nitro,
(d) oxo,
(e) C$_{1-6}$alkyl, optionally mono, di- or tri-substituted with halogen,
(f) C$_{1-6}$ alkoxy,
(g) C$_{3-6}$cycloalkyl,
(h) C$_{3-6}$cycloalkoxy,
(i) —NR$_{12}$R$_{13}$,
(j) —NH(C$_{3-6}$cycloalkyl),
(l) —N(C$_{3-6}$cycloalkyl)$_2$,
(m) —S(O)$_n$C$_{1-6}$alkyl,
(n) —S(O)$_n$C$_{3-6}$cycloalkyl,
(o) —S(O)$_n$aryl,
(p) —S(O)$_n$heteroaryl,
(q) aryl,
(r) heteroaryl,
(s) CN,
(t) —NHS(O)$_n$C$_{1-6}$alkyl,
(u) —NHS(O)$_n$aryl,
(v) —N(R$_{12}$)(S(O)$_n$)C$_{1-6}$alkylaryl,
(w) —N(R$_{12}$)C(O)R$_{13}$,
(x) —N(R$_{12}$)C(O)$_n$OR$_{13}$,
(y) —N(R$_{14}$)C(O)NR$_{12}$R$_{13}$,
(z) —C(O)NR$_{12}$R$_{13}$,
(aa) —C(O)R$_{12}$,
(bb) —C(O)OR$_{12}$,
(cc) —C$_{1-6}$alkylaryl, and
(dd) —C$_{1-6}$alkylheteroaryl;

wherein the alkyl of choices (e), (f), (m), (t), (v), (cc) and (dd) are each optionally mono- or di-substituted with substituents selected from halo, CF$_3$, hydroxyl, C$_{1-6}$ alkoxy, —NHC$_{1-6}$alkyl and —N(C$_{1-6}$alkyl)$_2$, and the aryl of choices (o), (q), (u), (v) and (cc) and the heteroaryl of choices (p), (r) and (dd) are each optionally mono or di-substituted with substituents selected halogen, hydroxyl, nitro, C$_{1-6}$alkyl, C$_{1-6}$ alkoxy, haloC$_{1-6}$alkyl, C$_{3-6}$cycloalkyl, C$_{3-6}$cycloalkoxy, —NH(C$_{3-6}$cycloalkyl), —N(C$_{3-6}$cycloalkyl)$_2$, —S(O)$_n$C$_{1-6}$alkyl, —S(O)$_n$C$_{3-6}$cycloalkyl, aryl, heteroaryl, and CN;

R$_{11}$ is selected from
(a) hydrogen,
(b) F,
(c) hydroxyl,
(d) —C$_{1-4}$alkyl,
(e) —S(O)$_n$C$_{1-4}$alkyl,
(f) —C(O)C$_{1-4}$alkyl,
(g) —OC$_{1-4}$alkyl,
(h) C$_{3-6}$ cycloalkyl,
(i) —S(O)$_n$C$_{3-6}$cycloalkyl,
(j) —OC$_{3-6}$cycloalkyl, and
(k) —C(O)C$_{3-6}$cycloalkyl, or R$_7$ and R$_{11}$ are joined together so that together with the atom to which they are attached there is formed an optionally mono-substituted 4, 5 or 6 membered saturated or partially unsaturated heterocycloalkyl ring having 1 or 2 heteroatoms selected from N, S and O, wherein the substituent is selected from halogen, hydroxyl, nitro, oxo, C$_{1-6}$alkyl, C$_{1-6}$ alkoxy, haloC$_{1-6}$alkyl, C$_{3-6}$cycloalkyl, C$_{3-6}$cycloalkoxy, —NR$_{12}$R$_{13}$, —NH(C$_{3-6}$cycloalkyl), —N(C$_{3-6}$cycloalkyl)$_2$, —S(O)$_n$C$_{1-6}$alkyl, —S(O)$_n$C$_{3-6}$cycloalkyl, aryl, heteroaryl, CN, —NHS(O)$_n$C$_{1-6}$alkyl, —NHS(O)$_n$aryl, —N(R$_{12}$)(S(O)$_n$)C$_{1-6}$alkylaryl and CO$_2$NR$_{12}$R$_{13}$; R$_{12}$ and R$_{13}$ are each independently (a) hydrogen,
(b) C$_{1-6}$alkyl,
(c) C$_{3-6}$ cycloalkyl,
(d) aryl,
(e) heteroaryl,
(f) —C$_{1-6}$alkylphenyl,
(g) —C$_{1-6}$alkylheteroaryl, and
(h) —S(O)$_n$phenyl, wherein the alkyl of choices (b), (f) and (g) are each optionally mono, di- or tri-substituted with halo and the aryl of choice (d), the phenyl of choices (f) and (h) and the heteroaryl choices (e) and (g) are each optionally mono or di-substituted with substituents selected from halogen, nitro, C$_{1-6}$alkyl, C$_{1-6}$ alkoxy, haloC$_{1-6}$alkyl, C$_{3-6}$cycloalkyl, C$_{3-6}$cycloalkoxy, —NH(C$_{1-3}$alkyl), —NH(C$_{3-6}$cycloalkyl), —N(C$_{1-3}$alkyl)$_2$, —N(C$_{3-6}$cycloalkyl)$_2$, —S(O)$_n$C$_{1-4}$alkyl, —S(O)$_n$C$_{3-6}$cycloalkyl, aryl, heteroaryl and CN; and R$_{14}$ is selected from hydrogen, and alkyl optionally mono, di- or tri substituted with halogen; and R$_{15}$ and R$_{16}$ are each independently selected from halogen, hydroxyl, nitro, C$_{1-6}$alkyl, —C$_{1-6}$alkylaryl, C$_{1-6}$ alkoxy, haloC$_{1-6}$alkyl, C$_{3-6}$cycloalkyl, C$_{3-6}$cycloalkoxy, —NR$_{12}$R$_{13}$, —NCONR$_{12}$R$_{13}$, —NH(C$_{3-6}$cycloalkyl), —N(C$_{1-6}$alkyl)$_2$, —N(C$_{3-6}$cycloalkyl)$_2$, —S(O)$_n$C$_{1-6}$alkyl, —S(O)$_n$C$_{3-6}$cycloalkyl, aryl, heteroaryl, CN, phenyloxy, —NHS(O)$_n$C$_{1-6}$alkyl, —NHS(O)$_2$aryl, —N(R$_{12}$)(S(O)$_n$)alkylaryl, —CONR$_{12}$R$_{13}$ and hydroxyC$_{1-6}$alkyl, wherein said aryl or said phenyl is optionally mono-substituted with halogen, nitro, C$_{1-6}$alkyl, C$_{1-6}$ alkoxy, halo C$_{1-6}$alkyl, C$_{3-6}$cycloalkyl, or C$_{3-6}$cycloalkoxy;

n is 0, 1, or 2.

Within this aspect there is a genus wherein Z is S or NH.
Within this genus there is a sub-genus wherein Z is S.

Within this aspect there is a genus wherein A1 is phenyl. In another aspect, A1 is a 6 membered heteroaromatic ring having 1 or 2 N atoms in the heteroaromatic ring.

Within this aspect there is a genus wherein A2 is phenyl. In another aspect, A2 is a 6 membered heteroaromatic ring having 1 or 2 N atoms in the heteroaromatic ring.

Within this genus there is a subgenus wherein A1 and A2 are each phenyl.

Within this aspect there is a genus wherein $R_1$ is selected from the group consisting of
(a) hydrogen,
(b) CN,
(c) $CF_3$,
(d) optionally substituted $C_{1-4}$alkyl, and
(e) optionally substituted $C_{1-4}$ alkoxy.

Within this genus there is a sub-genus wherein $R_1$ is $CF_3$.

In an alternative embodiment, $R_1$ is selected from the group consisting of
(a) hydrogen,
(b) hydroxyl,
(c) CN, and
(d) $CF_3$,
(e) optionally substituted $C_{1-4}$alkyl, and
(f) optionally substituted $C_{1-4}$ alkoxy.

Within this alternative embodiment there is an embodiment wherein $R_1$ is hydroxyl.

Within this aspect there is a genus wherein $R_2$ is hydrogen.
Within this aspect there is a genus wherein $R_3$ is hydrogen.
Within this aspect there is a genus wherein $R_4$ is hydrogen.
Within this aspect there is a genus wherein $R_2$, $R_3$ and $R_4$ are each hydrogen.
Within this aspect there is a genus wherein $R_6$ is hydroxyl.
Within this aspect there is a genus wherein $R_{11}$ is hydrogen.

Within this aspect there is a genus wherein $R_7$ and $R_8$ are joined together so that together with the nitrogen to which they are attached there is formed a 4, 5 or 6 membered saturated or unsaturated monocyclic heterocyclic ring or a 6 to 12 membered saturated or unsaturated bicyclic heterocylic ring, said monocyclic or bicyclic ring having 1 or 2 heteroatoms selected from N, $S(O)_n$ and O, and said monocyclic or bicyclic ring is optionally substituted with 1 to 4 substituents selected from $R_9$, $R_{10}$, $R_{15}$ and $R_{16}$.

Within this aspect there is a genus wherein the group

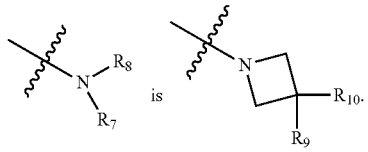

Within this genus there is a sub-genus wherein $R_9$ and $R_{10}$ joined together with the atoms connecting $R_9$ and $R_{10}$ form a $C_{3-6}$cycloalkyl, or a 4, 5 or 6 membered saturated or unsaturated monocyclic heterocycloalkyl ring or a 6 to 12 membered saturated or unsaturated bicyclic heterocycloalkyl ring, said monocyclic or bicyclic ring having 1 or 2 heteroatoms selected from N, $S(O)_n$ and O, and said $C_{3-6}$cycloalkyl, monocyclic or bicyclic heterocycloalkyl ring is optionally mono or di-substituted with substituents are independently selected from the group consisting of
(a) halogen,
(b) optionally substituted $C_{1-6}$alkyl,
(c) optionally substituted $C_{1-6}$ alkoxy,
(d) —$NR_{12}R_{13}$, (e) optionally substituted —$S(O)_nC_{1-6}$alkyl,
(f) optionally substituted —$S(O)_n$aryl,
(g) optionally substituted —$S(O)_n$heteroaryl,
(h) optionally substituted heteroaryl,
(i) —$N(R_{12})C(O)R_{13}$,
(j) —$N(R_{12})C(O)OR_{13}$,
(k) —$N(R_{14})C(O)NR_{12}R_{13}$,
(l) —$C(O)NR_{12}R_{13}$,
(m) —$C(O)R_{12}$, and
(n) —$C(O)OR_{12}$.

Within this genus there is a sub-genus wherein the group

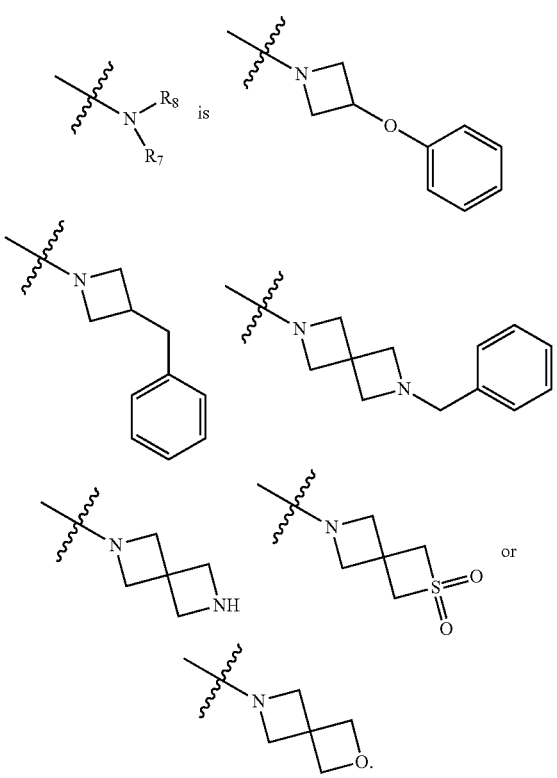

Within this genus there is a sub-genus wherein the group

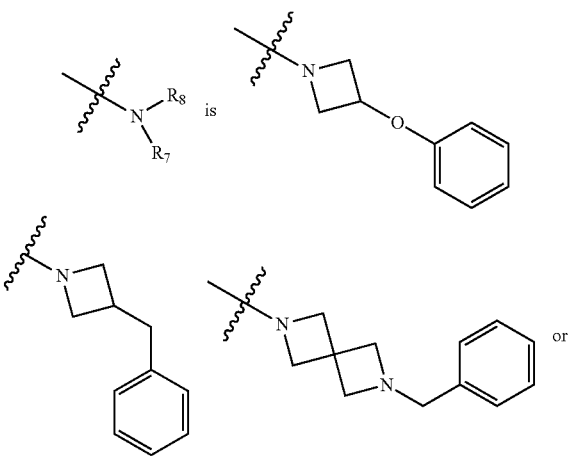

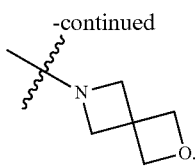

Within this aspect there is a genus of Formula Ia.

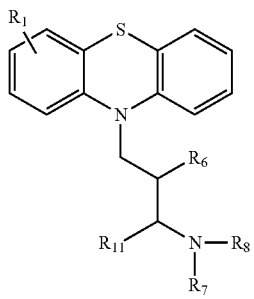

or a pharmaceutically acceptable salt thereof.

Within this genus there is a sub-genus wherein
(a) $R_1$ is $CF_3$,
(b) $R_6$ is hydroxyl, and
(c) $R_{11}$ is hydrogen.

Within this sub-genus there is a class of Formula Ib

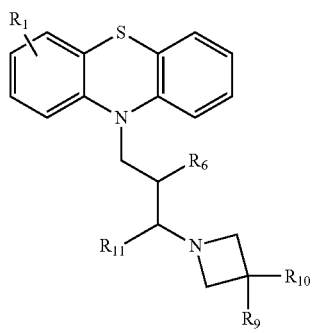

or a pharmaceutically acceptable salt thereof.

Within this class there is a sub-class wherein $R_9$ and $R_{10}$ joined together with the atoms connecting $R_9$ and $R_{10}$ form a $C_{3-6}$cycloalkyl, or a 4, 5 or 6 membered saturated or unsaturated monocyclic heterocycloalkyl ring or a 6 to 12 membered saturated or unsaturated bicyclic heterocycloalkyl ring, said monocyclic or bicyclic heterocycloalkyl ring having 1 or 2 heteroatoms selected from N, $S(O)_n$ and O, and said $C_{3-6}$cycloalkyl, monocyclic or bicyclic heterocycloalkyl ring is optionally mono or di-substituted with substituents are independently selected from the group consisting of
(a) halogen,
(b) optionally substituted $C_{1-6}$alkyl,
(c) optionally substituted $C_{1-6}$ alkoxy,
(d) —$NR_{12}R_{13}$,
(e) optionally substituted —$S(O)_nC_{1-6}$alkyl,
(f) optionally substituted —$S(O)_n$aryl,
(g) optionally substituted —$S(O)_n$heteroaryl,
(h) optionally substituted heteroaryl,
(i) —$N(R_{12})C(O)R_{13}$,
(j) —$N(R_{12})C(O)OR_{13}$,
(k) —$N(R_{14})C(O)NR_{12}R_{13}$,
(l) —$C(O)NR_{12}R_{13}$,
(m) —$C(O)R_{12}$, and
(n) —$C(O)OR_{12}$.

In one aspect, the compound of Formula I has the structure of Formula II:

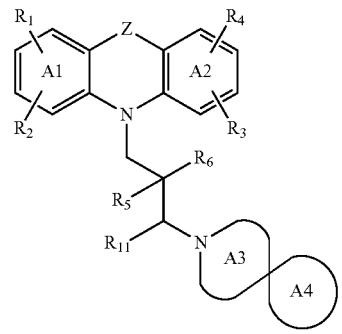

or a pharmaceutically acceptable salt thereof, wherein:
A3 is a 4, 5 or 6 membered saturated or unsaturated monocyclic heterocycloalkyl ring, said monocyclic heterocycloalkyl ring is optionally substituted with 1 to 2 substituents selected from $R_{15}$ and $R_{16}$;
A4 is a $C_{3-6}$cycloalkyl, or a 4, 5 or 6 membered saturated or unsaturated monocyclic heterocycloalkyl ring, said monocyclic heterocycloalkyl ring having 1 or 2 heteroatoms selected from N, $S(O)_n$ and O, and said $C_{3-6}$cycloalkyl, or monocyclic heterocycloalkyl ring is optionally mono or di-substituted with substituents that are independently selected from the group consisting of:
(a) halogen,
(b) hydroxyl,
(c) nitro,
(d) oxo,
(e) $C_{1-6}$ alkyl, optionally mono, di- or tri-substituted with halogen,
(f) $C_{1-6}$ alkoxy,
(g) $C_{3-6}$ cycloalkyl,
(h) $C_{3-6}$ cycloalkoxy,
(i) —$NR_{12}R_{13}$,
(j) —$NH(C_{3-6}$ cycloalkyl),
(l) —$N(C_{3-6}$ cycloalkyl)$_2$,
(m) —$S(O)_nC_{1-6}$ alkyl,
(n) —$S(O)_nC_{3-6}$cycloalkyl,
(o) —$S(O)_n$aryl,
(p) —$S(O)_n$heteroaryl,
(q) aryl,
(r) heteroaryl,
(s) CN,
(t) —$NHS(O)_nC_{1-6}$alkyl,
(u) —$NHS(O)_n$aryl,
(v) —$N(R_{12})(S(O)_n)C_{1-6}$alkylaryl,
(w) —$N(R_{12})C(O)R_{13}$,
(x) —$N(R_{12})C(O)OR_{13}$,
(y) —$N(R_{14})C(O)NR_{12}R_{13}$,
(z) —$C(O)NR_{12}R_{13}$,
(aa) —$C(O)R_{12}$,
(bb) —$C(O)OR_{12}$,
(cc) —$C_{1-6}$alkylaryl, and
(dd) —$C_{1-6}$alkylheteroaryl;

wherein the alkyl of choices (e), (f), (m), (t), (v), (cc) and (dd) are each optionally mono- or di-substituted with substituents selected from halo, CF$_3$, hydroxyl, C$_{1-6}$ alkoxy, —NHC$_{1-6}$alkyl and —N(C$_{1-6}$alkyl)$_2$, and the aryl of choices (o), (q), (u), (v) and (cc) and the heteroaryl of choices (p), (r) and (dd) are each optionally mono or di-substituted with substituents selected halogen, hydroxyl, nitro, C$_{1-6}$alkyl, C$_{1-6}$ alkoxy, haloC$_{1-6}$alkyl, C$_{3-6}$cycloalkyl, C$_{3-6}$cycloalkoxy, —NR$_{12}$R$_{13}$, —NH(C$_{3-6}$cycloalkyl), —N(C$_{3-6}$cycloalkyl)$_2$, —S(O)$_n$C$_{1-6}$alkyl, —S(O)$_n$C$_{3-6}$cycloalkyl, aryl, heteroaryl, and CN.

Within this aspect there is a genus of Formula IIa

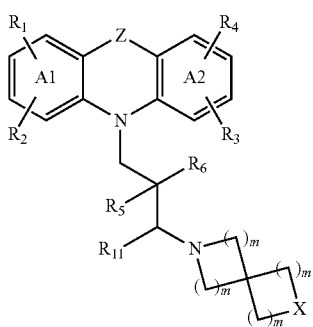

Formula IIa or a pharmaceutically acceptable salt thereof, wherein
X is N, S(O)$_n$ and O, where the N atom is substituted with hydrogen or with a substituent selected from the group consisting of:
(a) halogen,
(b) hydroxyl,
(c) nitro,
(d) oxo,
(e) C$_{1-6}$alkyl, optionally mono, di- or tri-substituted with halogen,
(f) C$_{1-6}$ alkoxy,
(g) C$_{3-6}$ cycloalkyl,
(h) C$_{3-6}$ cycloalkoxy,
(i) —NH$_{12}$R$_{13}$,
(j) —NH(C$_{3-6}$cycloalkyl),
(l) —N(C$_{3-6}$cycloalkyl)$_2$
(m) —S(O)$_n$C$_{1-6}$alkyl,
(n) —S(O)$_n$C$_{3-6}$cycloalkyl,
(o) —S(O)$_n$aryl,
(p) —S(O)$_n$heteroaryl,
(q) aryl,
(r) heteroaryl,
(s) CN,
(t) —NHS(O)$_n$C$_{1-6}$ alkyl,
(u) —NHS(O)$_n$aryl,
(v) —N(R$_{12}$)(S(O)$_n$)C$_{1-6}$ alkylaryl,
(w) —N(R$_{12}$)C(O)R$_{13}$,
(x) —N(R$_{12}$)C(O)OR$_{13}$,
(y) —N(R$_{14}$)C(O)NR$_{12}$R$_{13}$,
(z) —C(O)NR$_{12}$R$_{13}$,
(aa) —C(O)R$_{12}$,
(bb) —C(O)OR$_{12}$,
(cc) —C$_{1-6}$alkylaryl, and
(dd) —C$_{1-6}$alkylheteroaryl;
wherein the alkyl of choices (e), (f), (m), (t), (v), (cc) and (dd) are each optionally mono- or di-substituted with substituents selected from halo, CF$_3$, hydroxyl, C$_{1-6}$ alkoxy, —NHC$_{1-6}$alkyl and —N(C$_{1-6}$alkyl)$_2$, and the aryl of choices (o), (q), (u), (v) and (cc) and the heteroaryl of choices (p), (r) and (dd) are each optionally mono or di-substituted with substituents selected halogen, hydroxyl, nitro, C$_{1-6}$alkyl, C$_{1-6}$ alkoxy, halo C$_{1-6}$alkyl, C$_{3-6}$cycloalkyl, C$_{3-6}$cycloalkoxy, —NR$_{12}$R$_{13}$, —NH(C$_{3-6}$cycloalkyl), —N(C$_{3-6}$cycloalkyl)$_2$, —S(O)$_n$C$_{1-6}$alkyl, —S(O)$_n$C$_{3-6}$cycloalkyl, aryl, heteroaryl, and CN;

n is 0, 1, or 2; and
each m is independently selected from 1 and 2.

Within this aspect there is a genus wherein X is N, S(O)$_n$ and O, where the N atom is substituted with hydrogen or with a substituent selected from the group consisting of:
(a) C$_{1-6}$alkyl, optionally mono, di- or tri-substituted with halogen,
(b) C$_{3-6}$ cycloalkyl,
(c) —S(O)$_n$C$_{1-6}$alkyl,
(d) —S(O)$_n$C$_{3-6}$cycloalkyl,
(e) —S(O)$_n$aryl,
(f) —S(O)$_n$heteroaryl,
(g) aryl,
(h) heteroaryl,
(i) —C(O)R$_{12}$,
(j) —C$_{1-6}$alkylaryl, and
(k) —C$_{1-6}$alkylheteroaryl;
wherein the alkyl of choices (a), (c), (j) and (k) are each optionally mono- or di-substituted with substituents selected from halo, CF$_3$, hydroxyl, C$_{1-6}$ alkoxy, —NHC$_{1-6}$alkyl and —N(C$_{1-6}$alkyl)$_2$, and the aryl of choices (e), (g), and (j) and the heteroaryl of choices (f), (h) and (k) are each optionally mono- or di-substituted with substituents selected halogen, hydroxyl, nitro, C$_{1-6}$alkyl, C$_{1-6}$ alkoxy, C$_{3-6}$cycloalkyl, C$_{3-6}$cycloalkoxy, —NR$_{12}$R$_{13}$, —NH(C$_{3-6}$cycloalkyl), —N(C$_{3-6}$cycloalkyl)$_2$, —S(O)C$_{1-6}$alkyl, —S(O)$_n$C$_{3-6}$cycloalkyl, aryl, heteroaryl, and CN.

Within this aspect there is a genus wherein each m is 1. Within this aspect there is a genus wherein each m is 2.

Within this aspect there is a genus wherein X is N or O.

Any combination of the groups described above for the various variables is contemplated herein. Throughout the specification, groups and substituents thereof are chosen by one skilled in the field to provide stable moieties and compounds.

In another aspect the invention is directed to pharmaceutical compositions comprising a therapeutically effective amount of a compound of Formula I (including Formula Ia, Ib, II, and IIa) or a pharmaceutically acceptable salt thereof, as described above, and a pharmaceutically acceptable carrier.

It is understood that Formula Ia, Ib, II, and IIa are subsets of Formula I. Thus, any reference to Formula I Formula I also applies to Formula Ia, Ib, II, and IIa.

In another aspect of the invention the invention is directed to a method of promoting the generation, protection and/or survival of neurons in a patient in need thereof in such diseases, disorders or conditions as hearing loss, glaucoma, gloschizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, and abuse of neuro-active drugs, such as alcohol, opiates, methamphetamine, phencyclidine, and cocaine or other neurodegenerative diseases, comprising administration of a therapeutically effective amount of a compound of Formula I, or a pharmaceutically acceptable salt thereof, to the patient in need thereof In another aspect the invention is directed to a method of preventing or treating a neurodegenerative disease in a patient in need thereof comprising administration of a therapeutically effective amount of a compound of Formula I, or a pharmaceutically acceptable salt thereof, to the patient in need thereof.

In another aspect the invention is directed to a method of retarding or preventing mitochondrial apoptosis in a patient in need thereof comprising the administration of an effective amount of compound of Formula I, or a pharmaceutically acceptable salt thereof, to the patient in need thereof.

In another aspect the invention is directed to a method of preventing or treating a neurodegenerative disease in a patient in need thereof by inhibiting mitochondrial apoptosis mediated by the mitochondrial apoptosis-induced channel comprising administration of a therapeutically effective amount of a compound of Formula I, or a pharmaceutically acceptable salt thereof, to the patient in need thereof.

In another aspect the invention is directed to a method of inhibiting, blocking or disassembly of the mitochondrial apoptosis-induced channel in a patient in need thereof comprising administration of a therapeutically effective amount of a compound of Formula I, or a pharmaceutically acceptable salt thereof, to the patient in need thereof In one aspect, compounds disclosed herein inhibit or prevent the opening of MAC.

Definitions

The term "patient" includes mammals such as mice, rats, cows, sheep, pigs, rabbits, goats, horses, monkeys, dogs, cats, and humans. In certain embodiments, the mammal is a human.

The term "halo" or "halogen" refers to any radical of fluorine, chlorine, bromine or iodine.

The term "alkyl" refers to a saturated hydrocarbon chain that may be a straight chain or branched chain, containing the indicated number of carbon atoms. For example, $C_{1-6}$alkyl indicates that the group may have from 1 to 6 (inclusive) carbon atoms in it. Any atom can be optionally substituted, e.g., by one or more substitutents. Examples of alkyl groups include without limitation methyl, ethyl, n-propyl, isopropyl, n-butyl, sec-butyl and tert-butyl.

The term "haloalkyl" refers to an alkyl group, in which at least one hydrogen atom is replaced by halo. In some embodiments, more than one hydrogen atom (e.g., 2, 3, 4, 5, 6, 7, 8, 9, 10, 11, 12, 13, or 14) is replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl). Any atom can be optionally substituted, e.g., by one or more substituents.

As referred to herein, the term "alkoxy" refers to a group of formula —O(alkyl). Alkoxy can be, for example, methoxy, ethoxy, propoxy, isopropoxy, butoxy, iso-butoxy, sec-butoxy, pentoxy, 2-pentoxy, 3-pentoxy, or hexyloxy. Likewise, the term "thioalkoxy" refers to a group of formula —S(alkyl). The terms "haloalkoxy" and "thioalkoxy" refer to —O(haloalkyl) and —S(haloalkyl), respectively. The term "sulfhydryl" refers to —SH.

The term "aralkyl" refers to an alkyl moiety in which an alkyl hydrogen atom is replaced by an aryl group. One of the carbons of the alkyl moiety serves as the point of attachment of the aralkyl group to another moiety. Any ring or chain atom can be optionally substituted e.g., by one or more substituents. Non-limiting examples of "aralkyl" include benzyl, 2-phenylethyl, and 3-phenylpropyl groups.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl.

The term "heterocycle" or "heterocyclic", as used herein except where noted, represents a stable 4-, 5-, 6- of 7-membered monocyclic- or stable 6-, 7-, 8-, 9-, 10-, 11-, or 12-membered bicyclic heterocyclic ring system which is either saturated or unsaturated, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. In some embodiments, a heterocycle includes 1 to 3 heteroatoms selected from the group consisting of N, O or S. The heterocyclic ring may be attached at any heteroatom or carbon atom which results in the creation of a stable structure. In some embodiments, the heterocyclic group is saturated. In some embodiments, the heterocyclic group is not aromatic. Examples of heterocyclic groups include, but are not limited to, heterocycloalkyl and heteroaryl rings. Examples of heterocyclic groups include, but are not limited to, 2H-pyrrolyl, 3H-indolyl, 4H-quinolizinyl, acridinyl, benzo[b]thienyl, benzothiazolyl, beta-carbolinyl, carbazolyl, coumarinyl, chromenyl, cinnolinyl, dibenzo[b,d]furanyl, furazanyl, furyl, imidazolyl, imidizolyl, indazolyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, and xanthenyl.

The term "heterocycloalkyl", as used herein represents a stable 4-, 5-, 6- of 7-membered monocyclic- or stable 6-, 7-, 8-, 9-, 10-, 11-, or 12-membered bicyclic heterocyclic ring system which is either saturated or partially unsaturated, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. In some embodiments, "heterocycloalkyl" represents a stable 4-, 5-, 6- of 7-membered monocyclic ring system which is either saturated or partially unsaturated and consists of carbon atoms and 1 or 2 heteroatoms selected from the group consisting of N, O and S. Examples of such heterocycloalkyl groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be optionally substituted e.g., by one or more substituents. Cycloalkenyl moieties can include, e.g., cyclopentenyl, cyclohexenyl, cyclohexadienyl, or norbornenyl.

The term "cycloalkylene", as used herein, refers to a divalent monocyclic cycloalkyl group having the indicated number of ring atoms.

The term "heterocycloalkylene", as used herein, refers to a divalent monocyclic heterocycloalkyl group having the indicated number of ring atoms.

The term "aryl" as used herein, is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl. In some embodiments, an aryl is phenyl or napthyl. In some other embodiments, an aryl is phenyl.

The term "heteroaryl" or "heteroaromatic", as used herein except where noted, represents a stable 5, 6 or 7-membered monocyclic- or stable 9 or 10-membered fused bicyclic heterocyclic ring system which contains an aromatic ring, any ring of which may be saturated, such as piperidinyl, partially saturated, or unsaturated, such as pyridinyl, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof The term "acyl", as used herein, refers to those groups derived from an organic acid by removal of the hydroxy portion of the acid. Accordingly, acyl is meant to include, for example, acetyl, propionyl, butyryl, decanoyl, pivaloyl, benzoyl and the like.

Compound Forms and Salts

The compounds of this invention may contain one or more asymmetric centers and thus occur as racemates and racemic mixtures, enantiomerically enriched mixtures, single enantiomers, individual diastereomers and diastereomeric mixtures. The compounds of this invention may also be represented in multiple tautomeric forms. In such instances, the invention expressly includes all tautomeric forms of the compounds described herein, even though only a single tautomeric form may be represented. All such isomeric forms of such compounds are expressly included in the present invention.

The compounds of this invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids.

When the compound of the present invention is acidic, salts may be prepared from pharmaceutically acceptable non-toxic bases, including inorganic and organic acids. Such salts that may be prepared include a lithium salt, sodium salt, potassium salt, magnesium salt, calcium salt, dicyclohexylamine salt, N-methyl-D-glucamine salt, tris(hydroxymethyl)methylamine salt, arginine salt, lysine salt, and the like.

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

The compounds may be radiolabeled with radioactive isotopes, such as for example tritium, iodine-125 or carbon-14. All isotopic variations of the compounds of the invention, whether radioactive or not, are intended to be encompassed within the scope of the invention.

In some embodiments, hydrogen atoms of the compounds described herein may be replaced with deuterium atoms.

In some embodiments, compounds of Formula I are prepared as prodrugs. Prodrugs are generally drug precursors that, following administration to a subject and subsequent absorption, are converted to an active, or a more active species via some process, such as conversion by a metabolic pathway. Examples of prodrugs include $C_{1-6}$ alkyl esters of carboxylic acid groups, which, upon administration to a subject, are capable of providing active compounds.

Pharmaceutical Compositions

The term "pharmaceutically acceptable carrier" refers to a carrier or adjuvant that may be administered to a patient, together with a compound of this invention, or a pharmaceutically acceptable salt thereof, and which does not destroy the pharmacological activity thereof and is nontoxic when administered in doses sufficient to deliver a therapeutic amount of the compound.

The term "composition" as used herein is intended to encompass a product comprising the specified ingredients, as well as any product which results, directly or indirectly, from combination of the specified ingredients. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, or a pharmaceutically acceptable salt thereof, and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. For convenience, the total daily dosage may be divided and administered in portions during the day if desired.

Administration

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or administration by injection. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Dosage forms include from about 0.05 milligrams to about 2,000 milligrams (e.g., from about 0.1 milligrams to about 1,000 milligrams, from about 0.1 milligrams to about 500 milligrams, from about 0.1 milligrams to about 250 milligrams, from about 0.1 milligrams to about 100 milligrams, from about 0.1 milligrams to about 50 milligrams, or from about 0.1 milligrams to about 25 milligrams) of a compound of Formula I (and/or a compound of any of the other formulae described herein) or a salt (e.g., a pharmaceutically acceptable salt) thereof as defined anywhere herein. The dosage forms can further include a pharmaceutically acceptable carrier and/or an additional therapeutic agent.

In some embodiments, the compounds described herein can be coadministered with one or more other therapeutic agents. These may include, but are not limited to, antidepressant medications (including selective serotonin reuptake inhibitors, tricyclic antidepressants, monoamine oxidase inhibitors, and other antidepressant medications including but not limited to venlafaxine, nefazadone, bupropion, mirtazapine, lithium and trazodone) and drugs in the treatment of Alzheimer's disease such as acetylcholinesterase inhibitors (including but not limited to Aricept, Reminyl, and Exelon) as well NMDA modulators (including memantine (Nemenda)), and drugs useful in the treatment of Parkinson's disease such as LDOPA.

In certain embodiments, the additional agents may be administered separately, as part of a multiple dose regimen, from the compounds of this invention (e.g., sequentially, e.g., on different overlapping schedules with the administration of one or more compounds of Formula (I) (including any subgenera or specific compounds thereof)). In other embodiments, these agents may be part of a single dosage form, mixed together with the compounds of this invention in a single composition. In still another embodiment, these agents can be given as a separate dose that is administered at about the same time that one or more compounds of Formula (I) (including any subgenera or specific compounds thereof) are administered (e.g., simultaneously with the administration of one or more compounds of Formula (I) (including any subgenera or specific compounds thereof)). When the compositions of this invention include a combination of a compound of the formulae described herein and one or more additional therapeutic or prophylactic agents, both the compound and the additional agent can be present at dosage levels of between about 1 to 100%, and more preferably between about 5 to 95% of the dosage normally administered in a monotherapy regimen.

The compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions of this invention may be orally administered in any orally acceptable dosage form including, but not limited to, capsules, tablets, pills, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Uses

In one aspect, methods for treating (e.g., controlling, relieving, ameliorating, alleviating, or slowing the progression of) or methods for preventing (e.g., delaying the onset of or reducing the risk of developing) one or more diseases, disorders, or conditions caused by, or associated with, aberrant (e.g., insufficient) neurogenesis or accelerated neuron cell death in a patient in need thereof are featured. The methods include administering to the subject an effective amount of a compound of Formula (I) (and/or a compound of any of the other formulae described herein) or a salt (e.g., a pharmaceutically acceptable salt) thereof as defined anywhere herein to the patient. In another aspect, the use of a compound of Formula (I) (and/or a compound of any of the other formulae described herein) or a salt (e.g., a pharmaceutically acceptable salt) thereof as defined anywhere herein in the preparation of, or for use as, a medicament for the treatment (e.g., controlling, relieving, ameliorating, alleviating, or slowing the progression of) or prevention (e.g., delaying the onset of or reducing the risk of developing) of one or more diseases, disorders, or conditions caused by, or associated with, aberrant (e.g., insufficient) neurogenesis or exacerbated neuronal cell death is featured.

In another aspect of the invention the invention is directed to a method of promoting the generation, protection and/or survival of neurons in a patient in need thereof in such diseases, disorders or conditions such as hearing loss, glaucoma, gloschizophrenia, major depression, bipolar disorder, normal aging, epilepsy, traumatic brain injury, post-traumatic stress disorder, Parkinson's disease, Alzheimer's disease, Down syndrome, spinocerebellar ataxia, amyotrophic lateral sclerosis, Huntington's disease, stroke, radiation therapy, chronic stress, and abuse of neuro-active drugs, such as alcohol, opiates, methamphetamine, phencyclidine, and cocaine or other neurodegenerative diseases, comprising administration of a therapeutically effective amount of a compound of Formula I (and/or a compound of any of the other formulae described herein), or a pharmaceutically acceptable salt thereof, to the patient in need thereof.

In another aspect the invention is directed to a method of preventing or treating a neurodegenerative disease in a patient comprising administration of a therapeutically effective amount of a compound of Formula I, (and/or a compound of any of the other formulae described herein), or a pharmaceutically acceptable salt thereof, to the patient in need thereof In another aspect the invention is directed to a method of retarding or preventing mitochondrial apoptosis in a patient comprising the administration of an effective amount of compound of Formula I, (and/or a compound of any of the other formulae described herein), or a pharmaceutically acceptable salt thereof, to the patient in need thereof In another aspect the invention is directed to a method of preventing or treating a neurodegenerative disease by inhibiting mitochondrial apoptosis mediated by the mitochondrial apoptosis-induced channel in a patient comprising the administration of an effective amount of compound of Formula I, (and/or a compound of any of the other formulae described herein), or a pharmaceutically acceptable salt thereof, to the patient in need thereof.

In another aspect the invention is directed to a method of inhibiting, blocking or disassembly of the mitochondrial apoptosis-induced channel in a patient comprising the administration of an effective amount of compound of Formula I, (and/or a compound of any of the other formulae described herein), or a pharmaceutically acceptable salt thereof, to the patient in need thereof.

EXAMPLES

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the claims define the scope of the invention and that methods and structures within the scope of these claims and their equivalents be covered thereby.

Biological Function

Suitable assays which directly or indirectly detect neural survival, growth, development, function and/or generation are known in the art, including axon regeneration in rat models (e.g. Park et al., Science. 2008 Nov. 7; 322:963-6), nerve regeneration in a rabbit facial nerve injury models (e.g. Zhang et al., J Transl Med. 2008 Nov. 5; 6(1):67); sciatic nerve regeneration in rat models (e.g. Sun et al., Cell Mol Neurobiol. 2008 Nov. 6); protection against motor neuron degeneration in mice (e.g. Poesen et al. J. Neurosci. 2008 Oct. 15; 28(42):10451-9); rat model of Alzheimer's disease, (e.g. Xuan et al., Neurosci Lett. 2008 Aug. 8; 440(3):331-5); animal models of depression (e.g. Schmidt et al., e.g. Behav Pharmacol. 2007 September; 18(5-6):391-418; Krishnan et al. Nature 2008, 455, 894-902); and/or as exemplified herein.

The utility of the invention can be assessed by one or more of the following methods or other methods known in the art:

Mitochondrial Swelling

Certain mito-protective agents have been shown to prevent the calcium ion (100 µM)-stimulated swelling of isolated mitochondria. This swelling can be measured by detecting changes in absorbance at 540 nm using a plate-reader. This forms the basis for a simple screen for mito-protective agents. Mitochondria, from brain and liver, are isolated as described by Kristian (Current Protocols in Neuroscience 7.22.1-7.22.12, July 2010). Pelleted mitochondria are resuspended in a glutamate/malate (5 mM each) isotonic buffer and pipetted (90 µg/well) into a 96 well plate. Vehicle or compounds of interest are added to the mitochondria 15 mins prior to challenge with 1000 µM $CaCl_2$. Absorbance at 540 nm is monitored with a plate-reader and a reduction of the calcium-stimulated swelling is interpreted as mito-protection.

HeLa Cytochrome C Release Assay

Inhibition of the pro-apoptotic protein cytochorome C by a compound of Formula I (and/or a compound of any of the other formulae described herein), was evaluated in mitochondria isolated from HeLa cells. In the assay, 10-20 million HeLa cells were resuspended in assay buffer (70 mM sucrose; 230 mM mannitol; 1 mM EDTA; 5 mM HEPES, pH 7 with KOH) containing protease inhibitor cocktail (Sigma P-8340) and treated with 1.5 µg/million cells digitonin for 5 minutes at 4° C. Cells were pelleted by centrifugation and washed twice with assay buffer containing 0.5% BSA. Cells were resuspended in assay buffer and homogenized with a Dounce homogenizer (60 strokes) on ice. Intact cells were removed by centrifugation (1000×g, 10 min) and the supernatant centrifuged (8,500×g, 10 min) The mitochondrial pellet was resuspended in assay buffer to achieve a protein concentration of 0.333 µg/ml. 15 µl of Test compound (at 5× dilution) was combined with 45 µl mitochondria and incubated for 15 min at RT. Cytochrome C release was initiated with 15 µl t-Bid (final conc=25 nM) and the reaction continued for 30 min at RT. Samples were then centrifuged (12,000×g, 10 min) and 50 µl of the supernatant analyzed for cytochrome C content by ELISA (R & D Systems, #DCTCO).

BAX Liposome Assay

Inhibition of BAX oligomerization and pore formation was evaluated using a liposome assay preparation. To do so, 30% 1,2-dioleoyl-sn-glycero-3-phosphate and 70% 1,2-dioleoyl-sn-glycero-3-phosphocholine (Avanti Polar Lipids, Alabaster, Ala.) were mixed in chloroform followed by evaporation at 37° C. under nitrogen (Saito et al., 2000). Liposomes were then rehydrated with agitation in buffer containing 50 mM 10 kD-dextran carboxyfluorescein (dextran-CF, Invitrogen, Carlsbad, Calif.), 100 mM KCl, 1 mM EDTA and 20 mM HEPES at pH 7.4. Liposomes were then sized using 5 freeze-thaw cycles, 5 minutes in a sonication bath, followed by 3 passages through a 5 µm syringe filter and 5 passages through a 0.2 µm syringe filter. Free dextran-CF was removed by Sepharose S-300 size exclusion chromatography (GE Healthcare, Piscataway, N.J.). Recombinant GST-Bax protein (Abnova, Taipei, Taiwan) was activated by incubating for 30 minutes in 2% octyglucoside in the presence or absence of compound X in a 96-well plate. Liposomes were then added to the activated GST-Bax (final concentration 10 nM). Carboxyfluorescein release from liposomes was measured by excitation with 497 nm light and the $A_{520}$ monitored for 15 minutes.

In Vitro Human SHSY5Y Survival Assay

In order to determine if compounds effect cell survival, we tested them in an in vitro assay using the human neuroblastoma cell line SH-SY5Y. SH-SY5Y human neuroblastoma cells treated with retinoic acid for 5 days produce a homogeneous population of neuronal differentiated cells that are strictly dependant on BDNF for their survival. SH-SY5Y cells are plated on 96-well collagen coated plates and incubated for 24 hours. Retinoic acid is then added and incubated on the cells for 5 days. After 5 days, media with retinoic acid is removed and replaced with serum free media+/−compound. Each plate includes basal media (negative) and BDNF (positive) controls. The cells are then fixed with paraformaldehyde (3.7%) and stained with the nuclear marker Hoechst and the neuronal marker beta-Tubulin III. The plate is imaged using the In Cell Analyzer 2000™. Each well is imaged in 9 different spots throughout the well. The images are analyzed with a custom-designed algorithm using the In Cell Developer™ software. Data is averaged per compound concentration and calculated as a background subtracted percent of positive control.

Identification of Pro-Neurogenic Compounds

An in vivo neurogenesis assay was conducted in order to determine whether compounds can stimulate the birth of new neurons within the CNS.

Male C57B16 mice 3-5 months of age were housed in groups of 4. Compounds were prepared as a suspension in 0.5% methylcellulose and dosed by oral gavage in a volume of 10 ml/kg Animals were dosed once daily for 7 consecutive days. Control animals received 0.5% methylcellulose only. During compound administration, animals were intraperitoneally (i.p.) injected daily with the thymidine analog, bromodeoxyuridine (BrdU, 50 mg/kg), as a means of identifying the birth and survival of proliferating neural precursor cells in the hippocampus. Twenty-four hours after the final injection of BrdU, animals were deeply anesthetized with sodium pentobarbital (100 mg/kg i.p.) and then perfused with ice cold saline solution followed by 10% formalin. Brains were removed and 40 µm slices collected for immunohistochemistry with an antibody to BrdU. Images were taken with an InCell 2000. Neurogenesis was quantified by counting the number of BrdU positive cells in every 5th slice throughout the entire rostral-caudal extent of the hippocampal dentate gyrus sub granular zone. The number of positive cells was normalized against the volume of the dentate gyrus.

Identification of Compounds that Enhance Survival of Newborn Neurons

Compounds that promote neurogenesis may do so by enhancing the survival of new born neurons. By altering the administration timing of BrdU we can assess neuron survival.

Male C57B16 mice 3-5 months of age were housed in groups of 4. Compounds were prepared as a suspension in 0.5% methylcellulose and dosed by oral gavage in a volume of 10 ml/kg Animals were dosed once daily for 30 consecutive days. Control animals received 0.5% methylcellulose only. Animals were exposed to a single pulse of BrdU (50 mg/kg, i.p.) on day 2 of the 30 day dosing period. Following the 30 day period of compound administration, animals were deeply anesthetized with sodium pentobarbital (100 mg/kg i.p.) and then perfused with ice cold saline solution followed by 10% formalin. Brains were removed and 40 µm slices collected for immunohistochemistry with an antibody to BrdU. Images were taken with an InCell 2000. Neurogenesis was quantified by counting the number of BrdU positive cells in every 5th slice throughout the entire rostral-caudal extent of the hippocampal dentate gyrus sub granular zone. The number of positive cells was normalized against the volume of the dentate gyrus Animals were perfused and sacrificed. Dissected brain tissue was fixed, embedded, sectioned, stained with antibodies to BrdU, and evaluated by light microcopy as a means of quantifying survival of newborn neural precursor cells localized to the subgranular layer of the dentate gyrus. Every fifth section throughout the entire rostral-caudal extent of the hippocampus was analyzed, and the total number of BrdU+ cells was normalized against the measured volume of the dentate gyrus.

Biological Data:

Neuronal survival assay: The compound of Example 1 demonstrated an $EC_{50}$ of 509 nM (n=2).

BAX Liposome Assay: The compound of Example 1 demonstrated an $IC_{50}$ of 24.6 µM.

HeLa Cytochrome C release assay: The compound of Example 3 demonstrated 93% inhibition of cytochrome C release at a concentration of 10 µM. The compound of Example 4 demonstrated 27% inhibition of cytochrome C release at a concentration of 10 µM.

Synthesis

The compounds of the invention are prepared by the following general scheme:

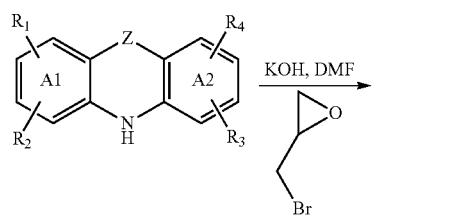

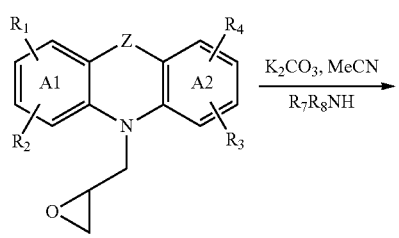

Compounds may also be prepared using the synthetic methods outlined in US 2011/0003836 A1 and WO 01/29028 A1.

Example 1

Synthesis of (±)-1-(2-oxa-6-azaspiro[3.3]heptan-6-yl)-3-(2-(trifluoromethyl)-10H-phenothiazin-10-yl)propan-2-ol

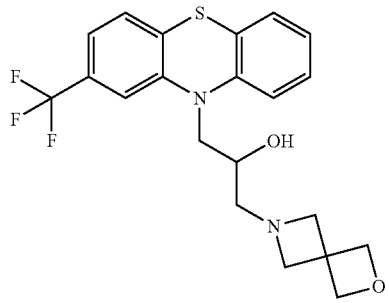 [SMILES: OC(CN1CC2(COC2)C1)CN1c2ccccc2Sc2ccc(C(F)(F)F)cc21]

Step 1: (±)-10-(oxiran-2-ylmethyl)-2-(trifluoromethyl)-10H-phenothiazine

To a solution of 2-(trifluoromethyl)-10H-phenothiazine (5.0 g, 18.8 mmol) and DMF (15 mL) at RT was added finely powdered KOH (2.1 g, 37.5 mmol) and (±)-epibromohydrin (3.9 mL, 48.9 mmol). The reaction mixture was stirred at RT for 48 h. Once no starting material was observed by analytical LCMS, EtOAC (250 mL) and brine (250 mL) were added. The organic layer was separated, and the aqueous layer was washed with EtOAC (3×100 mL). The combined organic extracts were washed with brine (2×100 mL), dried over $MgSO_4$, and concentrated to afford the title compound.

Step 2: To a solution of (±)-10-(oxiran-2-ylmethyl)-2-(trifluoromethyl)-10H-phenothiazine and 2-methyl-2-propanol (2 mL) was added finely powdered KOH (62 mg, 11 mmol) and 2-oxa-6-azaspiro[3.3]heptane hemioxalate salt (37 mg, 0.38 mmol) The reaction mixture was heated to 65° C. for 12 h. Once no starting material was observed by analytical LCMS, EtOAC (50 mL) and brine (50 mL) were added. The organic layer was separated, and the aqueous layer was washed with EtOAC (3×100 mL). The combined organic extracts were washed with brine (2×25 mL), dried over $MgSO_4$, and concentrated. The residue was purified by flash chromatography on silica gel (0-100% EtOAc in hexanes) to afford the title compound. LCMS m/z 423 (M+H)

Example 2

Synthesis of (±)-1-morpholino-3-(2-(trifluoromethyl)-10H-phenothiazin-10-yl)propan-2-ol

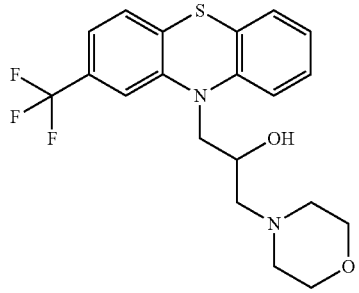 [SMILES: OC(CN1CCOCC1)CN1c2ccccc2Sc2ccc(C(F)(F)F)cc21]

Step 1: Utilizing the procedure outline in Example 1, Step 2, (±)-10-(oxiran-2-ylmethyl)-2-(trifluoromethyl)-10H-phenothiazine and 2-methyl-2-propanol (127 mg, 0.39 mmol) was reacted with morpholine (41 µL, 0.48 mmol) to afford the title compound. LCMS m/z 411 (M+H)

Example 3

Synthesis of (±)-1-(2,6-diazaspiro[3.3]heptan-2-yl)-3-(2-(trifluoromethyl)-10H-phenothiazin-10-yl)propan-2-ol

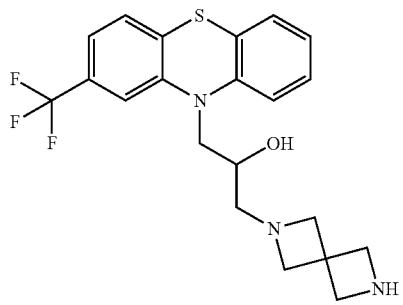 [SMILES: OC(CN1CC2(CNC2)C1)CN1c2ccccc2Sc2ccc(C(F)(F)F)cc21]

Step 1: Synthesis of (±)-tert-butyl 6-(2-hydroxy-3-(2-(trifluoromethyl)-10H-phenothiazin-10-yl)propyl)-2,6-diazaspiro[3.3]heptane-2-carboxylate. Utilizing the procedure outline in Example 1, Step 2, (±)-10-(oxiran-2-ylmethyl)-2-(trifluoromethyl)-10H-phenothiazine and 2-methyl-2-propanol (142 mg, 0.44 mmol) was reacted with tert-butyl 2,6-diazaspiro[3.3]heptane-2-carboxylate hemioxalate salt (130 mg, 0.53 mmol) to afford the title compound.

Step 2: A solution of (±)-tert-butyl 6-(2-hydroxy-3-(2-(trifluoromethyl)-10H-phenothiazin-10-yl)propyl)-2,6-diazaspiro[3.3]heptane-2-carboxylate and $CH_2Cl_2$ was reacted with HCl (0.13 mL, 0.52 mmol, 4.0N solution in dioxane). The reaction mixture was stirred for 12 h. Once no starting material was observed by analytical LCMS, the reaction mixture was concentrated. The residue was purified by flash chromatography on silica gel (0-100% EtOAc in hexanes) to afford the title compound. LCMS m/z 422 (M+H)

Example 4

Synthesis of 10-(3-(2,6-diazaspiro[3.3]heptan-2-yl)propyl)-2-(trifluoromethyl)-10H-phenothiazine

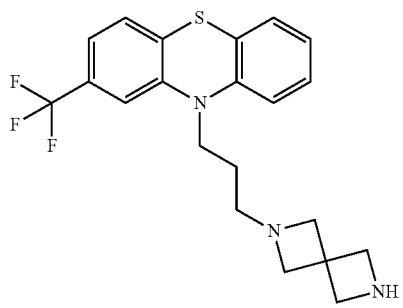 [SMILES: FC(F)(F)c1ccc2c(c1)N(CCCN1CC3(CNC3)C1)c1ccccc1S2]

Step 1: Synthesis of 10-(3-chloropropyl)-2-(trifluoromethyl)-10H-phenothiazine. A solution of 2-(trifluoromethyl)-10H-phenothiazine (2.04 g, 7.6 mmol) and DMF (16 mL) was mixed with $CS_2CO_3$ (7.5 g, 22.9 mmol) and 1-bromo-3-chloropropane (1.1 mL, 11.5 mmol) The reaction mixture was heated at 65° C. for 12 h. Once no starting material was observed by analytical LCMS, EtOAC (250 mL) and brine (250 mL) were added. The organic layer was separated, and the aqueous layer was washed with EtOAC (3×100 mL). The combined organic extracts were washed with brine (2×100 mL), dried over $MgSO_4$, and concentrated to afford the title compound.

Step 2: Synthesis of 10-(3-iodopropyl)-2-(trifluoromethyl)-10H-phenothiazine. A solution of 10-(3-chloropropyl)-2-(trifluoromethyl)-10H-phenothiazine was mixed with acetone (50 mL) and NaI (4.0 g, 26 mmol) and heated at 55° C. for 48 h. Once no starting material was observed by analytical LCMS, the reaction mixture was partitioned between $CH_2Cl_2$ (100 mL) and an aqueous solution of $Na_2S_2O_3$ (20 ml). The organic layer is dried with $MgSO_4$ and concentrated to afford the title compound.

Step 3: Synthesis of tert-butyl 6-(3-(2-(trifluoromethyl)-10H-phenothiazin-10-yl)propyl)-2,6-diazaspiro[3.3]heptane-2-carboxylate. A solution of 10-(3-iodopropyl)-2-(trifluoromethyl)-10H-phenothiazine (148 mg, 0.34 mmol) and MeCN (2 mL) is mixed with $K_2CO_3$ (141 mg, 1.0 mmol) and tert-butyl 2,6-diazaspiro[3.3]heptane-2-carboxylate hemioxalate salt (83 mg, 0.34 mmol) The reaction vessel was sealed and heated at 65° C. for 12 h. Once no starting material was observed by analytical LCMS, EtOAC (50 mL) and brine (50 mL) were added. The organic layer was separated, and the aqueous layer was washed with EtOAC (3×50 mL). The combined organic extracts were washed with brine (25 mL), dried over $MgSO_4$, and concentrated to afford the title compound.

Step 4: tert-Butyl 6-(3-(2-(trifluoromethyl)-10H-phenothiazin-10-yl)propyl)-2,6-diazaspiro[3.3]heptane-2-carboxylate was processed as in example 3 step 2 to afford the title compound. LCMS m/z 406 (M+H)

Example 5

Synthesis of (±)-1-(2-(ethylthio)-10H-phenothiazin-10-yl)-3-(2-oxa-6-azaspiro[3.3]heptan-6-yl)propan-2-ol

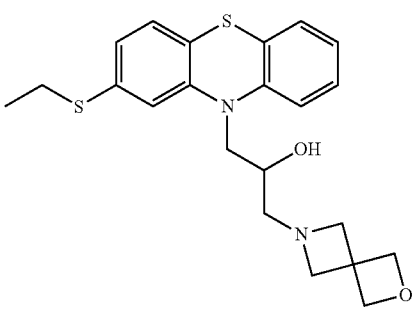 [SMILES: CCSc1ccc2c(c1)N(CC(O)CN1CC3(COC3)C1)c1ccccc1S2]

Utilizing the procedure outlined in Example 1, 2-(ethylthio)-10H-phenothiazine was employed to obtain the title compound. LCMS m/z 415 (M+H)

Example 6

Synthesis of (±)-1-(2-methoxy-10H-phenothiazin-10-yl)-3-(2-oxa-6-azaspiro[3.3]heptan-6-yl)propan-2-ol

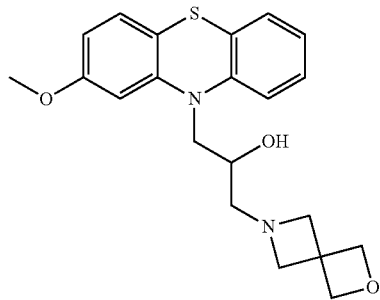 [SMILES: COc1ccc2c(c1)N(CC(O)CN1CC3(COC3)C1)c1ccccc1S2]

Utilizing the procedure outlined in Example 1, 2-methoxy-10H-phenothiazine was employed to obtain the title compound. LCMS m/z 385 (M+H)

Example 7

Synthesis of (±)-1-(2-chloro-10H-phenothiazin-10-yl)-3-(2-oxa-6-azaspiro[3.3]heptan-6-yl)propan-2-ol

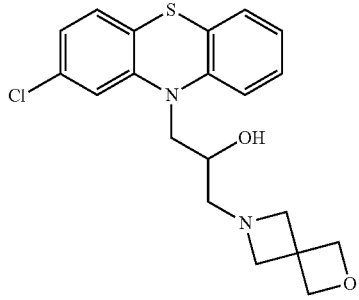 [SMILES: OC(CN1CC2(COC2)C1)CN1c2ccccc2Sc2ccc(Cl)cc21]

Utilizing the procedure outlined in Example 1, 2-chloro-10H-phenothiazine was employed to obtain the title compound. LCMS m/z 389 (M+H)

Example 8

Synthesis of (±)-1-(10H-phenoxazin-10-yl)-3-(2-oxa-6-azaspiro[3.3]heptan-6-yl)propan-2-ol

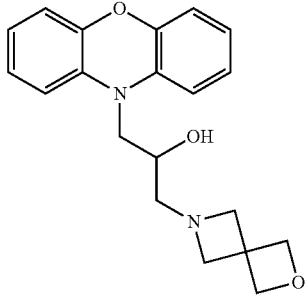 [SMILES: OC(CN1CC2(COC2)C1)CN1c2ccccc2Oc2ccccc21]

Utilizing the procedure outlined in Example 1, 10H-phenoxazine is employed to obtain the title compound.

Example 9

Synthesis of (±) 1-(2,7-dichloroacridin-10(9H)-yl)-3-(2-oxa-6-azaspiro[3.3]heptan-6-yl)propan-2-ol

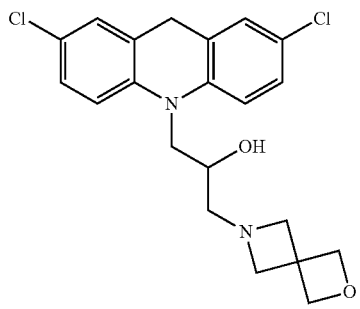 [SMILES: OC(CN1CC2(COC2)C1)CN1c2ccc(Cl)cc2Cc2cc(Cl)ccc21]

Utilizing the procedure outlined in Example 1, 2,7-dichloro-9,10-dihydroacridine is employed to obtain the title compound.

What is claimed is:

1. A compound of Formula I

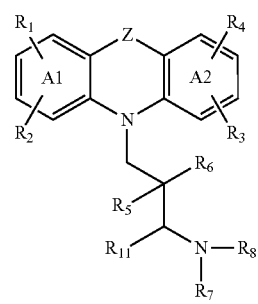

or a pharmaceutically acceptable salt thereof, wherein:
A1 and A2 are each independently phenyl or a 6 membered heteroaromatic ring having 1, 2 or 3 N atoms in the heteroaromatic ring;
Z is selected from the group consisting of S and $S(O)_2$;
R is selected from the group consisting of
(a) $CF_3$,
(b) $C_{1-6}$alkyl,
(c) —$S(O)_2C_{1-4}$alkyl,
(d) —$C(O)C_{1-4}$alkyl,
(e) $C_{3-6}$cycloalkyl,
(f) —$C(O)C_{3-6}$cycloalkyl,
(g) —$S(O)_2C_{3-6}$cycloalkyl,
(h) —$C(O)_2C_{1-4}$alkyl,
(i) —$C(O)_2C_{3-6}$cycloalkyl,
(j) aryl, and
(k) heteroaryl,
wherein the alkyl portion of choices (b), (c), (d) and (h) and the cycloalkyl portion of choices (e), (f), (g) and (i) is optionally substituted with halo, and
wherein the aryl of choice (j) and the heteroaryl of choice (k) are each optionally mono or di-substituted with substituents selected from halogen, nitro, $C_{1-6}$alkyl, $C_{1-6}$alkoxy, halo $C_{1-6}$alkyl, $C_{3-6}$cycloalkyl, $C_{3-6}$cycloalkoxy, —$NH(C_{1-6}$alkyl), —$NH(C_{3-6}$cycloalkyl), —$N(C_{1-6}$alkyl)$_2$, —$N(C_{3-6}$cycloalkyl)$_2$, —$S(O)_nC_{1-6}$alkyl, —$S(O)_nC_{3-6}$cycloalkyl and CN;

$R_1$, $R_2$, $R_3$ and $R_4$ are each independently selected from the group consisting of
(a) hydrogen,
(b) halogen,
(c) CN,
(d) $CF_3$,
(e) $C_{1-6}$alkyl,
(f) $C_{1-6}$alkoxy,
(g) —$S(O)_n C_{1-6}$alkyl,
(h) —$NH(C_{1-6}$alkyl),
(i) —$N(C_{1-6}$alkyl$)_2$,
(j) —$NHC(O)(C_{1-6}$alkyl),
(k) —$NHS(O)_2 C_{1-6}$alkyl,
(l) —$NHS(O)_2$aryl,
(m) —$C_{3-6}$cycloalkyl,
(n) —$C_{3-6}$cycloalkoxy,
(o) —$S(O)_n C_{3-6}$cycloalkyl,
(p) —$NH(C_{3-6}$cycloalkyl),
(q) —$N(C_{3-6}$cycloalkyl$)_2$,
(r) —$NHS(O)_2 C_{3-6}$cycloalkyl,
(s) —$C(O)C_{3-6}$cycloalkyl,
(t) —$C(O)C_{1-6}$alkyl,
(u) aryl,
(v) heteroaryl,
(w) —$S(O)_n NR_{12}R_{13}$, and
(x) —$C(O)NR_{12}R_{13}$,
wherein the alkyl portion of choices (e), (f), (g), (h), (i), (j), (k) and (t) and the cycloalkyl portion of choices (m), (o), (p), (q), (r) and (s) is optionally substituted with halo, and
wherein aryl choice (u) and heteroaryl of choice (v) are each optionally mono or di-substituted with substituents selected from halogen, nitro, $C_{1-6}$alkyl, $C_{1-6}$alkoxy, halo $C_{1-6}$alkyl, $C_{3-6}$cycloalkyl, $C_{3-6}$cycloalkoxy, —NH($C_{1-6}$alkyl), NH($C_{3-6}$cycloalkyl), —N($C_{1-6}$alkyl$)_2$, —N($C_{3-6}$cycloalkyl$)_2$, —$S(O)_n C_{1-6}$alkyl, —$S(O)_n C_{3-6}$cycloalkyl and CN;
$R_5$ is selected from the group consisting of:
(a) hydrogen,
(b) F,
(c) $C_{1-6}$alkyl, and
(d) $C_{3-6}$cycloalkyl;
$R_6$ is selected from the group consisting of:
(a) hydrogen,
(b) F,
(c) hydroxyl,
(d) —$C_{1-6}$alkyl,
(e) —$S(O)_n C_{1-6}$alkyl,
(f) —$C(O)C_{1-6}$alkyl,
(g) —$OC_{1-6}$alkyl,
(h) —$NH_2$,
(i) —$NH(C_{1-6}$alkyl),
(j) —$N(C_{1-6}$alkyl$)_2$,
(k) $C_{3-6}$cycloalkyl,
(l) —$C(O)C_{3-6}$cycloalkyl,
(m) —$S(O)_n C_{3-6}$cycloalkyl,
(n) —$OC_{3-6}$cycloalkyl,
(o) —$NH(C_{3-6}$cycloalkyl), and
(p) —$N(C_{3-6}$cycloalkyl$)_2$,
or $R_5$ and $R_6$ together with the carbon to which they are attached forms a $C_{3-6}$cycloalkyl, or an optionally monosubstituted 4, 5 or 6 membered saturated or partially unsaturated heterocycloalkyl ring having 1 or 2 heteroatoms selected from N, $S(O)_n$ and O, wherein the substituent is selected from halogen, hydroxyl, nitro, oxo, $C_{1-6}$alkyl, $C_{1-6}$cycloalkyl, halo$C_{1-6}$alkyl, $C_{3-6}$cycloalkyl, $C_{3-6}$cycloalkoxy, —NH($C_{3-6}$cycloalkyl), —N($C_{3-6}$cycloalkyl$)_2$, —$S(O)_n C_{1-6}$alkyl, —$S(O)_n C_{3-6}$cycloalkyl, aryl, heteroaryl, CN, —$NHS(O)_n C_{1-6}$alkyl, —$NHS(O)_n$aryl, —$N(R_{12})(S(O)_n)C_{1-6}$alkylaryl and —$C(O)_2 NR_{12}R_{13}$;
the group

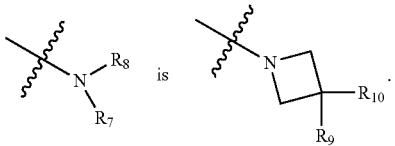

is $R_9$ is hydrogen; and
$R_{10}$ is selected from halogen, hydroxyl, nitro, —$C_{1-6}$alkylaryl, $C_{1-6}$alkoxy, halo$C_{1-6}$alkyl, $C_{3-6}$cycloalkyl, $C_{3-6}$cycloalkoxy, —$NR_{12}R_{13}$, —$NCONR_{12}R_{13}$, —NH($C_{3-6}$cycloalkyl), —N($C_{1-6}$alkyl$)_2$, —N($C_{3-6}$cycloalkyl$)_2$, —$S(O)_n C_{1-6}$alkyl, —$S(O)_n C_{3-6}$cycloalkyl, aryl, heteroaryl, CN, aryloxy, —$NHS(O)_n C_{1-6}$alkyl, —$NHS(O)_2$aryl, —$N(R_{12})(S(O)_n)$alkylaryl, —$CONR_{12}R_{13}$ and hydroxy$C_{1-6}$alkyl, wherein said aryl is optionally mono-substituted with halogen, nitro, $C_{1-6}$alkyl, $C_{1-6}$alkoxy, halo $C_{1-6}$alkyl, $C_{3-6}$cycloalkyl, or $C_{3-6}$cycloalkoxy;
or $R_9$ and $R_{10}$ are joined together with the atoms connecting $R_9$ and $R_{10}$ to form a $C_{3-6}$cycloalkyl, or a 4, 5 or 6 membered saturated or unsaturated monocyclic heterocyclic ring or a 6 to 12 membered saturated or unsaturated bicyclic heterocylic ring, said monocyclic or bicyclic ring having 1 or 2 heteroatoms selected from N, $S(O)_n$ and O, and said $C_{3-6}$cycloalkyl, monocyclic or bicyclic heterocyclic ring is optionally mono or di-substituted with substituents that are independently selected from the group consisting of:
(a) halogen,
(b) hydroxyl,
(c) nitro,
(d) oxo,
(e) $C_{1-6}$alkyl, optionally mono, di- or tri-substituted with halogen,
(f) $C_{1-6}$alkoxy,
(g) $C_{3-6}$cycloalkyl,
(h) $C_{3-6}$cycloalkoxy,
(i) —$NR_{12}R_{13}$,
(j) —NH($C_{3-6}$cycloalkyl),
(l) —N($C_{3-6}$cycloalkyl$)_2$,
(m) —$S(O)_n C_{1-6}$alkyl,
(n) —$S(O)_n C_{3-6}$cycloalkyl,
(o) —$S(O)_n$aryl,
(p) —$S(O)_n$heteroaryl,
(q) aryl,
(r) heteroaryl,
(s) CN,
(t) —$NHS(O)_n C_{1-6}$alkyl,
(u) —$NHS(O)_n$aryl,
(v) —$N(R_{12})(S(O)_n)C_{1-6}$alkylaryl,
(w) —$N(R_{12})C(O)R_{13}$,
(x) —$N(R_{12})C(O)OR_{13}$,
(y) —$N(R_{14})C(O)NR_{12}R_{13}$,
(z) —$C(O)NR_{12}R_{13}$,
(aa) —$C(O)R_{12}$,
(bb) —$C(O)OR_{12}$,
(cc) —$C_{1-6}$alkylaryl, and
(dd) —$C_{1-6}$alkylheteroaryl;

wherein the alkyl of choices (e), (f), (m), (t), (v), (cc) and (dd) are each optionally mono- or di-substituted with substituents selected from halo, $CF_3$, hydroxyl, $C_{1-6}$alkoxy, —$NHC_{1-6}$alkyl and —$N(C_{1-6}$alkyl$)_2$, and the aryl of choices (o), (q), (u), (v) and (cc) and the heteroaryl of choices (p), (r) and (dd) are each optionally mono or di-substituted with substituents selected halogen, hydroxyl, nitro, $C_{1-6}$alkyl, $C_{1-6}$alkoxy, halo$C_{1-6}$alkyl, $C_{3-6}$cycloalkyl, $C_{3-6}$cycloalkoxy, —$NR_{12}R_{13}$, —$NH(C_{3-6}$cycloalkyl), —$N(C_{3-6}$cycloalkyl$)_2$, —$S(O)_n$$C_{1-6}$alkyl, —$S(O)_n$$C_{3-6}$cycloalkyl, aryl, heteroaryl, and CN;

$R_{11}$ is selected from
(a) hydrogen,
(b) F,
(c) hydroxyl,
(d) —$C_{1-4}$alkyl,
(e) —$S(O)_n$$C_{1-4}$alkyl,
(f) —$C(O)C_{1-4}$alkyl,
(g) —$OC_{1-4}$alkyl,
(h) $C_{3-6}$cycloalkyl,
(i) —$S(O)_n$$C_{3-6}$cycloalkyl,
(j) —$OC_{3-6}$cycloalkyl, and
(k) —$C(O)C_{3-6}$cycloalkyl $R_{12}$ and $R_{13}$ are each independently
(a) hydrogen,
(b) $C_{1-6}$alkyl,
(c) $C_{3-6}$cycloalkyl,
(d) aryl,
(e) heteroaryl,
(f) —$C_{1-6}$alkylphenyl,
(g) —$C_{1-6}$alkylheteroaryl, and
(h) —$S(O)_n$phenyl, wherein the alkyl of choices (b), (f) and (g) are each optionally mono-, di- or tri-substituted with halo and the aryl of choice (d), the phenyl of choices (f) and (h) and the heteroaryl choices (e) and (g) are each optionally mono or di-substituted with substituents selected from halogen, nitro, $C_{1-6}$alkyl, $C_{1-6}$alkoxy, halo$C_{1-6}$alkyl, $C_{3-6}$cycloalkyl, $C_{3-6}$cycloalkoxy, —$NH(C_{1-3}$alkyl), $NH(C_{3-6}$cycloalkyl), —$N(C_{1-3}$alkyl$)_2$, —$N(C_{3-6}$cycloalkyl$)_2$, —$S(O)_n$$C_{1-4}$alkyl, $S(O)_n$$C_{3-6}$cycloalkyl, aryl, heteroaryl and CN; and $R_{14}$ is selected from hydrogen, and alkyl optionally mono-, di- or tri-substituted with halogen; and
n is 0, 1, or 2.

2. The compound according to claim 1, or a pharmaceutically acceptable salt thereof, wherein $R_9$ and $R_{10}$ joined together with the atoms connecting $R_9$ and $R_{10}$ form a $C_{3-6}$cycloalkyl, or a 4, 5 or 6 membered saturated or unsaturated monocyclic heterocycloalkyl ring or a 6 to 12 membered saturated or unsaturated bicyclic heterocycloalkyl ring, said monocyclic or bicyclic ring having 1 or 2 heteroatoms selected from N, $S(O)_n$ and O, and said $C_{3-6}$cycloalkyl, monocyclic or bicyclic heterocycloalkyl ring is optionally mono or di-substituted with substituents independently selected from the group consisting of
(a) halogen,
(b) optionally substituted $C_{1-6}$alkyl,
(c) optionally substituted $C_{1-6}$alkoxy,
(d) —$NR_{12}R_{13}$,
(e) optionally substituted —$S(O)_n$$C_{1-6}$alkyl,
(f) optionally substituted —$S(O)_n$aryl,
(g) optionally substituted —$S(O)_n$heteroaryl,
(h) optionally substituted heteroaryl,
(i) —$N(R_{12})C(O)R_{13}$,
(j) —$N(R_{12})C(O)OR_{13}$,
(k) —$N(R_{14})C(O)NR_{12}R_{13}$,
(l) —$C(O)NR_{12}R_{13}$,
(m) —$C(O)R_{12}$, and
(n) —$C(O)OR_{12}$.

3. The compound of claim 1 or a pharmaceutically acceptable salt thereof, wherein the group

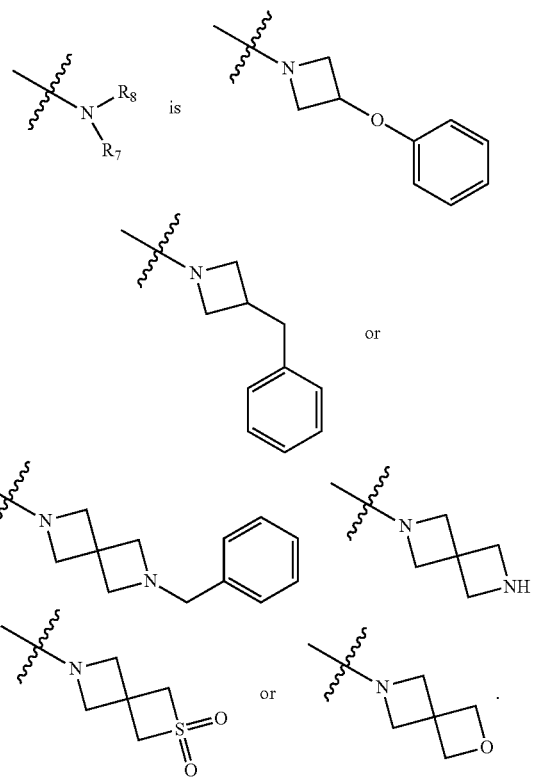

4. The compound according to claim 1, wherein the compound of Formula I has the structure of Formula Ia:

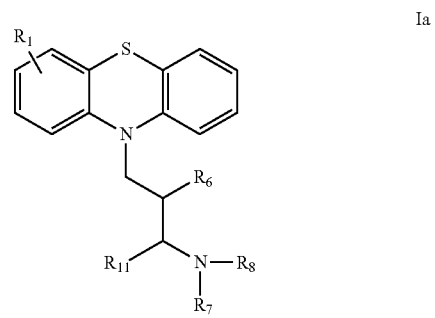

or is a pharmaceutically acceptable salt thereof.

5. The compound according to claim 4, or a pharmaceutically acceptable salt thereof, wherein:
(a) $R_1$ is $CF_3$,
(b) $R_6$ is hydroxyl, and
(c) $R_{11}$ is hydrogen.

6. The compound according to claim 5, or a pharmaceutically acceptable salt thereof, wherein $R_9$ and $R_{10}$ joined together with the atoms connecting $R_9$ and $R_{10}$ form a $C_{3-6}$cycloalkyl, or a 4, 5 or 6 membered saturated or unsaturated monocyclic heterocycloalkyl ring or a 6 to 12 membered saturated or unsaturated bicyclic heterocycloalkyl ring, said monocyclic or bicyclic heterocycloalkyl rings having 1 or 2 heteroatoms selected from N, S(O)$_n$ and O, and said C$_{3-6}$cycloalkyl, monocyclic or bicyclic heterocycloalkyl ring is optionally mono or di-substituted with substituents are independently selected from the group consisting of
(a) halogen,
(b) optionally substituted C$_{1-6}$alkyl,
(c) optionally substituted C$_{1-6}$alkoxy,
(d) —NR$_{12}$R$_{13}$,
(e) optionally substituted —S(O)$_n$C$_{1-6}$alkyl,
(f) optionally substituted —S(O)$_n$aryl,
(g) optionally substituted —S(O)$_n$heteroaryl,
(h) optionally substituted heteroaryl,
(i) —N(R$_{12}$)C(O)R$_{13}$,
(j) —N(R$_{12}$)C(O)OR$_{13}$,
(k) —N(R$_{14}$)C(O)NR$_{12}$R$_{13}$,
(l) —C(O)NR$_{12}$R$_{13}$,
(m) —C(O)R$_{12}$, and
(n) —C(O)OR$_{12}$.

7. The compound according to claim 1 selected from 1-(2-oxa-6-azaspiro[3.3]heptan-6-yl)-3-(2-(trifluoromethyl)-10H-phenothiazin-10-yl)propan-2-ol, 1-(2,6-diazaspiro[3.3]heptan-2-yl)-3-(2-(trifluoromethyl)-10H-phenothiazin-10-yl)propan-2-ol, 10-(3-(2,6-diazaspiro[3.3]heptan-2-yl)propyl)-2-(trifluoromethyl)-10H-phenothiazine, 1-(2-(ethylthio)-10H-phenothiazin-10-yl)-3-(2-oxa-6-azaspiro[3.3]heptan-6-yl)propan-2-ol, 1-(2-methoxy-10H-phenothiazin-10-yl)-3-(2-oxa-6-azaspiro[3.3]heptan-6-yl)propan-2-ol, 1-(2-chloro-10H-phenothiazin-10-yl)-3-(2-oxa-6-azaspiro[3.3]heptan-6-yl)propan-2-ol, and

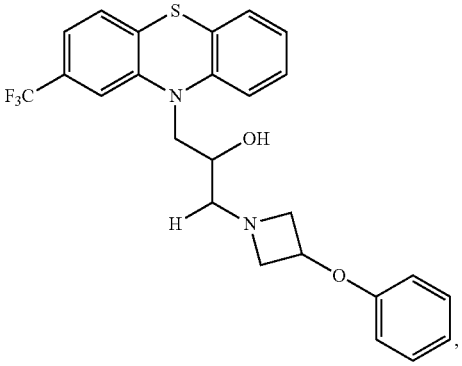 [SMILES: OC(CN1CC(Oc2ccccc2)C1)CN1c2ccccc2Sc2ccc(C(F)(F)F)cc21]

or a pharmaceutically acceptable salt of any one of the preceding compounds.

8. A pharmaceutical composition comprising a compound according to claim 1, or a pharmaceutically acceptable salt thereof, and a pharmaceutically acceptable carrier.

* * * * *